(12) United States Patent
Ehlers et al.

(10) Patent No.: US 11,832,847 B2
(45) Date of Patent: Dec. 5, 2023

(54) EXPANDERS FOR ROD RETRACTION

(71) Applicant: Stryker European Operations Holdings LLC, Kalamazoo, MI (US)

(72) Inventors: Andrew Edward Ehlers, Monroe, NY (US); Steven F. Krause, Oakland, NJ (US); Charles L. Bush, Jr., Wayne, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 115 days.

(21) Appl. No.: 17/236,356

(22) Filed: Apr. 21, 2021

(65) Prior Publication Data

US 2021/0275218 A1    Sep. 9, 2021

Related U.S. Application Data

(63) Continuation of application No. 15/999,176, filed on Aug. 17, 2018, now Pat. No. 11,020,145.

(60) Provisional application No. 62/546,847, filed on Aug. 17, 2017.

(51) Int. Cl.
*A61B 17/34* (2006.01)
*A61B 17/02* (2006.01)

(52) U.S. Cl.
CPC ........ *A61B 17/3439* (2013.01); *A61B 17/025* (2013.01); *A61B 17/0206* (2013.01); *A61B 17/0218* (2013.01); *A61B 2017/0256* (2013.01)

(58) Field of Classification Search
CPC ............ A61B 17/3439; A61B 17/0218; A61B 17/025
See application file for complete search history.

(56) References Cited

U.S. PATENT DOCUMENTS

| | | | |
|---|---|---|---|
| 1,157,202 A | 10/1915 | Bates et al. |
| 3,731,673 A | 5/1973 | Halloran |
| 3,749,088 A | 7/1973 | Kohlmann |
| 3,782,370 A | 1/1974 | McDonald |

(Continued)

FOREIGN PATENT DOCUMENTS

| FR | 2807313 A1 | 10/2001 |
|---|---|---|
| WO | 2018039228 A1 | 3/2018 |

OTHER PUBLICATIONS

Bush et al., U.S. Appl. No. 62/546,841, titled "Independent Rod Suspension" filed Aug. 17, 2017.

(Continued)

*Primary Examiner* — Si Ming Ku
(74) *Attorney, Agent, or Firm* — Duane Morris LLP

(57) ABSTRACT

In one embodiment, an expander set includes a first and second expander. The first expander includes an outer surface having a first engagement feature and a groove and the second expander includes an inside surface having a second engagement feature adapted to engage with the first engagement feature. The inside surface of the second expander is shaped to correspond to a portion of the outer surface of the first expander. Additionally, the groove on the outer surface of the first expander is sized and shaped to accommodate a rod of a retraction system such that when the first expander is advanced within the retraction system, the rod remains within the groove. When the first and second expanders are engaged with one another, they define an oblong cross-section.

15 Claims, 19 Drawing Sheets

(56) References Cited

U.S. PATENT DOCUMENTS

| | | | |
|---|---|---|---|
| 3,807,393 | A | 4/1974 | McDonald |
| 3,965,890 | A | 6/1976 | Gauthier |
| 4,616,635 | A | 10/1986 | Caspar et al. |
| 5,052,373 | A | 10/1991 | Michelson |
| 5,941,777 | A | 8/1999 | Moser et al. |
| 5,944,658 | A | 8/1999 | Koros et al. |
| 7,056,321 | B2 | 6/2006 | Pagliuca et al. |
| 7,261,688 | B2 | 8/2007 | Smith et al. |
| 7,374,534 | B2 | 5/2008 | Dalton |
| 7,390,298 | B2 | 6/2008 | Chu |
| 7,645,232 | B2 | 1/2010 | Shluzas |
| 7,879,009 | B1 | 2/2011 | Haddock et al. |
| 7,909,761 | B2 | 3/2011 | Banchieri et al. |
| 7,985,179 | B2 | 7/2011 | Gephart et al. |
| 8,192,463 | B2 | 6/2012 | McLoughlin |
| 8,435,175 | B2 | 5/2013 | McMahon et al. |
| 8,480,576 | B2 | 7/2013 | Sandhu |
| 8,608,652 | B2 | 12/2013 | Voegele et al. |
| 8,702,600 | B2 | 4/2014 | Perrow |
| 8,801,608 | B2 | 8/2014 | Hardenbrook |
| 8,870,760 | B2 | 10/2014 | Heiges et al. |
| 8,894,574 | B2 | 11/2014 | Ellman |
| 8,992,558 | B2 | 3/2015 | Stone et al. |
| 9,028,522 | B1 | 5/2015 | Prado |
| 9,138,137 | B2 | 9/2015 | Deshmukh et al. |
| 9,339,263 | B2 * | 5/2016 | Fenn .................. A61B 1/32 |
| 9,408,598 | B1 | 8/2016 | Fantini et al. |
| 9,554,789 | B2 | 1/2017 | Overes et al. |
| 9,615,818 | B2 | 4/2017 | Baudouin et al. |
| 9,737,290 | B2 | 8/2017 | Fatone et al. |
| 9,808,232 | B2 | 11/2017 | Heiman et al. |
| 2006/0195017 | A1 | 8/2006 | Shluzas et al. |
| 2007/0060939 | A1 | 3/2007 | Lancial et al. |
| 2007/0208366 | A1 | 9/2007 | Pellegrino et al. |
| 2009/0024158 | A1 | 1/2009 | Viker |
| 2009/0105546 | A1 | 4/2009 | Hestad et al. |
| 2010/0280627 | A1 | 11/2010 | Hanes, II |
| 2012/0022575 | A1 | 1/2012 | Mire et al. |
| 2012/0245431 | A1 | 9/2012 | Baudouin et al. |
| 2013/0289355 | A1 | 10/2013 | Sandhu |
| 2014/0039264 | A1 * | 2/2014 | Heiman ............ A61B 17/025 600/210 |
| 2014/0142420 | A1 | 5/2014 | Jackson, III |
| 2014/0276869 | A1 | 9/2014 | Tatsumi |
| 2014/0303666 | A1 | 10/2014 | Heiman et al. |
| 2015/0164496 | A1 | 6/2015 | Karpowicz et al. |
| 2015/0342589 | A1 | 12/2015 | Bootwala |
| 2016/0081681 | A1 | 3/2016 | Waugh et al. |
| 2016/0120532 | A1 | 5/2016 | Donald |
| 2016/0361052 | A1 | 12/2016 | Reimels |
| 2017/0007228 | A1 | 1/2017 | Costabile |
| 2017/0021147 | A1 * | 1/2017 | Predick .............. A61B 17/3421 |
| 2017/0071589 | A1 | 3/2017 | Simonson |
| 2017/0340317 | A1 | 11/2017 | Fatone et al. |
| 2018/0064450 | A1 | 3/2018 | Jackson, III |

OTHER PUBLICATIONS

Krause et al., U.S. Appl. No. 62/546,780, titled "Lateral Access Alignment Guide and Rigid Arm" filed Aug. 17, 2017.
Popejoy et al., U.S. Appl. No. 62/546,796, titled "Bridges and Lighting for Lateral Access" filed Aug. 17, 2017.
Popejoy et al., U.S. Appl. No. 62/650,579, titled "Lateral Access Shim and Rod Lighting and Tissue Retraction" filed Mar. 30, 2018.
Extended European Search Report for EP Application No. 18189068.2, dated Jan. 23, 2019.

* cited by examiner

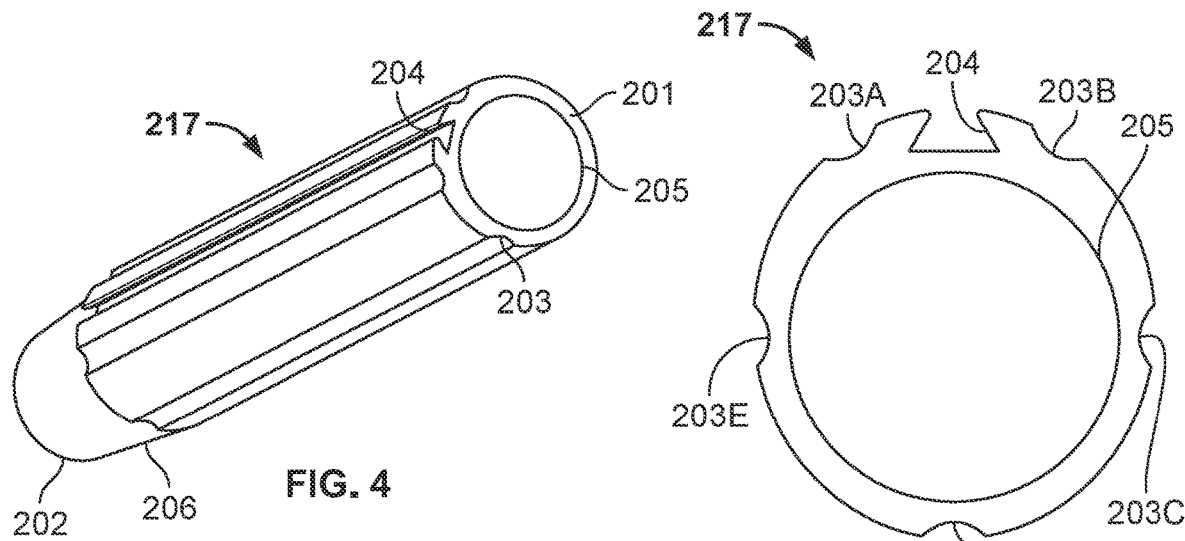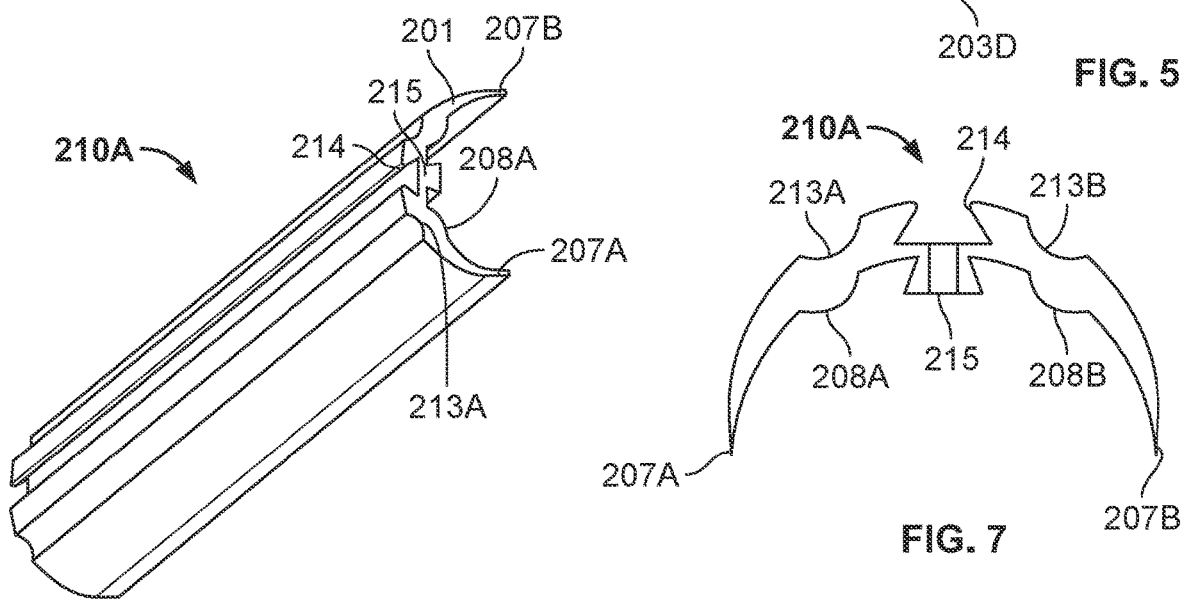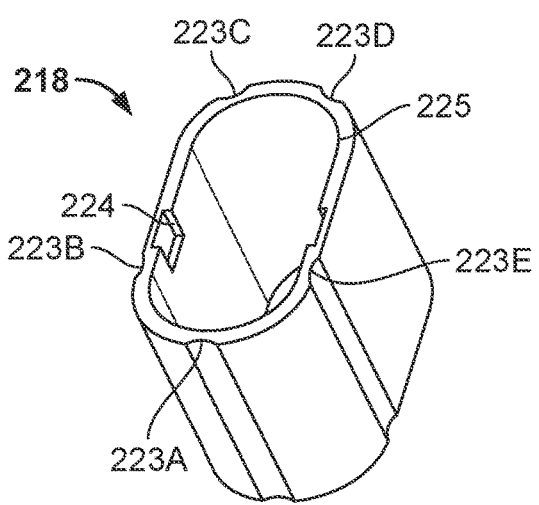

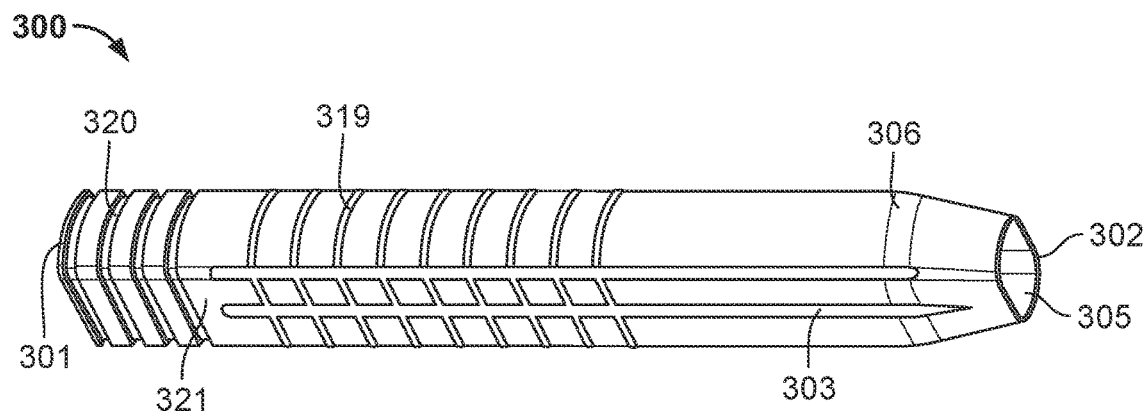
FIG. 9
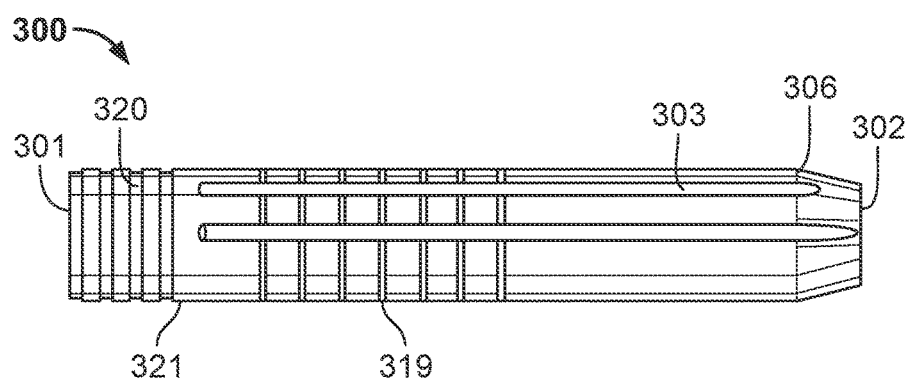 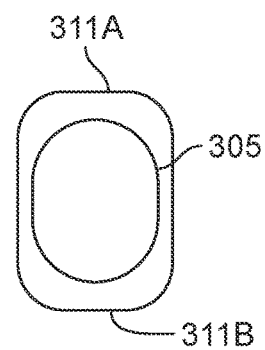
FIG. 10　　　　　　　　FIG. 11
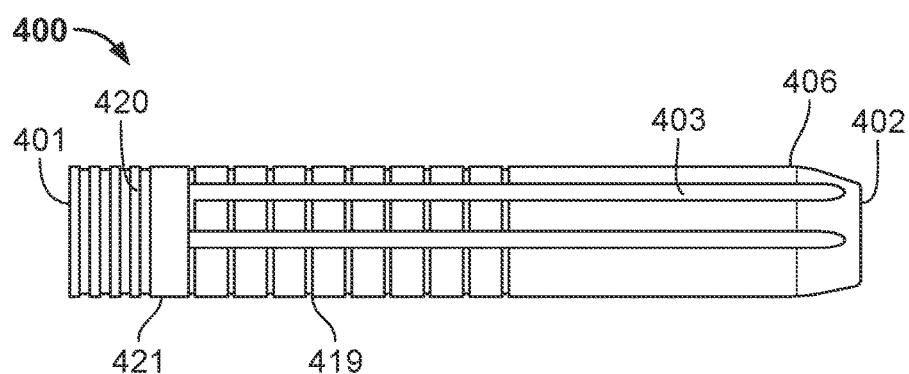 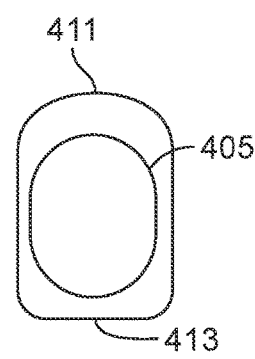
FIG. 12　　　　　　　　FIG. 13

EXPANDERS FOR ROD RETRACTION

CROSS-REFERENCE TO RELATED APPLICATIONS

The present application is a continuation of U.S. application Ser. No. 15/999,176, filed Aug. 17, 2018, which claims the benefit of the filing date of U.S. Provisional Patent Application No. 62/546,847, filed on Aug. 17, 2017, the disclosures of which are hereby incorporated by reference herein in its entirety. Additionally, the disclosure of commonly owned WO2018/039228, filed Aug. 22, 2017 ("the '228 Publication"), is hereby incorporated by reference herein in its entirety and the disclosures of commonly owned U.S. Provisional Patent Application Nos. 62/546,841 ("the '841 Application"), 62/546,780 ("the '780 Application"), 62/546,796 ("the '796 Application") and 62/650,579 ("the '579 Application") are also hereby incorporated by reference herein in their entirety.

BACKGROUND OF THE INVENTION

Spinal implants are commonly utilized in spinal procedures designed to treat spinal maladies. Such implants are used, for example, to immobilize and fuse adjacent vertebral bodies. This often plays a critical role in addressing spinal diseases or injury, or otherwise treating pain in a patient.

Various techniques have been developed and are often employed to access the spine during a spinal implant implantation procedure. These techniques are often dictated by the type of implant being utilized. For example, the spine may be accessed using a posterior approach, an anterior approach, or a lateral approach. Among these, a lateral approach is advantageous in that a portal to access a surgical site may be larger than with other approaches, thus allowing for a larger implant to be used, which experience over time has shown tends to improve the overall outcome of the procedure.

One method for implanting lateral implants is via a lateral trans-psoas approach. This typically involves the creation of an incision on the lateral side of the patient. Thereafter, a path to a surgical site, i.e., the vertebral bodies, is systematically created. One technique to accomplish this involves the use of sequential dilators, where an insertion of each dilator over another progressively increases the size of a tissue area displaced by the dilators. The area created by such dilation is circular and will expand the incision in all directions. Thus, such approaches to sequential dilation unnecessarily open the incision in the cephalad and caudal directions. Moreover, circular portals into a surgical site are not often an optimal shape to conduct a procedure. Additionally, these types of approaches present risks in that the procedure provides less control for the avoidance of nerves during the increase in the pathway to the vertebrae.

Thus, there is a need for improved structures, systems and methods for creating access to the surgical site.

BRIEF SUMMARY OF THE INVENTION

In one aspect, the present disclosure relates to expansion sets. In one embodiment, an expansion set includes a first expander and a second expander. The first expander has an outer surface with a first engagement feature and a groove. The second expander has an inside surface having a second engagement feature adapted to engage with the first engagement feature, the inside surface shaped to correspond to a portion of the outer surface of the first expander. The groove on the outer surface of the first expander is sized and shaped to accommodate a rod of a retraction system such that when the first expander is advanced within the retraction system, the rod remains within the groove. The first and second expanders are sized so that, when engaged with one another, the combination defines an oblong cross-section.

In one embodiment, the expander set includes a third expander releasably engagable with the second expander. In a variant, the third expander is configured to increase a size of the expander set in a single axis when engaged with the second expander. In another embodiment, the outer surface of the first expander further comprises a second groove located on a second portion of the outside surface that is unobstructed by the second expander when the second expander is engaged with the first expander. In yet another embodiment, the inside surface of the second expander includes a protrusion corresponding to the groove on the outside surface of the first expander. In a variant, the second expander includes an outside surface with a second groove and a third engagement feature, the second groove having the same shape as the first groove.

In one embodiment, the expander set includes a cylindrical tube having a smooth outer surface corresponding to an inner surface of the first expander. In another embodiment, the expander set includes a tissue retaining ring having an oblong shape and an opening therein. The opening is sized so that a plurality of expanders including the first and second expanders are disposable within the opening. An outer surface of the tissue retaining ring includes a second groove located in alignment with the first groove of the first expander such that a rod engagable with the first groove is also engagable with the second groove when the tissue retaining ring is inserted over the expanders. In a variant, the tissue retaining ring includes a recess on an inner surface defining the opening, the recess shaped to accommodate the securement of a ring configured to generate light.

In another aspect, the present disclosure relates to expansion devices. In one embodiment, an expansion device is configured to retract a plurality of rods and includes a central core member and a channel member. The central core member is configured to vary in length when actuated by an actuating mechanism. The channel member is adjacent to the central core member and is connected to the central core member by an interconnecting structure. The interconnecting structure rotates about a connection with the central core member when a length of the central core member increases or decreases. The rotation of the interconnecting structure causes the respective channel member connected to the interconnecting structure to move relative to the central core member in a direction transverse to a length of the central core member.

In one embodiment, the central core member includes an upper portion and a lower portion, the upper portion moving relative to the lower portion in response to actuation by the actuation mechanism in the form of a handle. In a variant, the interconnecting structure includes a first arm connected to the upper portion of the central core member at one end and an upper end of the channel member at another end. The interconnecting structure also includes a second arm connected to the lower portion of the central core member at one end and a lower end of the channel member at another end. Each arm is configured to pivot relative to the central core member in response to movement of the upper portion relative to the lower portion. In a further variant, the ends of the first and second arms connected to the channel member move further from or closer to the central core member as the upper portion moves relative to the lower portion. In yet another variant, the expansion device includes a second channel member connected to the central core member by third and fourth arms. Each arm extends transversely from a length of the central core member such that a plane through the third and fourth arms is at an angle relative to a plane through the first and second arms. The arms may be structured so that the first and second arms each have a first length and the third and fourth arms each have a second length where the first length is different from the second length. In yet another variant, the expansion device is structured so that when the channel members are in an open position at their furthest distance from central core member, a perimeter defined by a totality of the channel members is of a non-circular shape.

In one embodiment, the channel member of the expansion device is parallel to the central core member at a minimum and maximum length of the central core member, and at lengths in between. In another embodiment, the interconnecting structure of the expansion device is configured so that a change in the length of the central core member corresponds to a lateral movement of the channel member relative to the central core member.

In yet another aspect, the present disclosure relates to a method of creating a portal in a body of a patient. In one embodiment, the method includes the following steps: advancing a retractor including a plurality of rods into the body of the patient; inserting a first expander into the retractor so that grooves on the first expander surface engage the rods, the rods moving apart from one another increasing a size of a portal defined by an area between the rods; and, engaging a second expander with the first expander by placing the second expander over the first expander so that a groove on an outer surface of the second expander engages at least one rod but not all of the rods engaged by the first expander. The insertion of the second expander increases the size of the portal in a single direction.

In one embodiment, the method includes an insertion step after advancing the retractor and prior to inserting the first expander. The insertion step involves inserting a tube in between the rods so that a tapered end of the tube is the insertion end. In another embodiment, the engaging step includes engaging a first engagement feature of the first expander with a second engagement feature of the second expander so that a position of the second expander relative to the first expander remains constant as second expander is advanced into the body. In another embodiment, an additional engaging step is performed that involves engaging a third expander with the second expander after inserting the second expander. The engagement of the third expander with the second expander causes a rod in the groove of the second expander to be pushed into a groove in the third expander. A displacement of the rod due to insertion of the third expander being in the same direction as displacement of the rod by the second expander.

In one embodiment, the method includes an insertion step that involves inserting a tissue retaining ring over a plurality of expanders including at least the first and second expander engaged with one another. The tissue retaining ring includes an opening therethrough sized to correspond to a combined cross-section of the plurality of expanders. The tissue retaining ring further retracts the rods relative to the combined cross-section of the plurality of expanders and enlarges the portal. In another embodiment, the method includes an insertion step after advancing the rods and prior to inserting the first expander. The insertion step includes inserting a sleeve assisted expander including a tapered tube and a sleeve thereon in a withdrawn position until a tapered end of the tube is inserted to a depth approximately matching the rods. Insertion of the sleeve assisted expander concomitantly increases the size of the portal. Once inserted, the sleeve of the expander is advanced over the tube to further increase the size of the portal.

BRIEF DESCRIPTION OF THE DRAWINGS

A more complete appreciation of the subject matter of the present disclosure and of the various advantages thereof may be realized by reference to the following detailed description in which reference is made to the accompanying drawings in which:

FIGS. 4-5 are perspective and section views, respectively, of a base expander of the expander set shown in FIG. 2.

FIGS. 6-7 are perspective and section views, respectively, of a shim of the expander set shown in FIG. 2.

FIG. 8 is a perspective view of a tissue retaining ring according to one embodiment of the present disclosure which supplements the expander set shown in FIG. 2.

FIG. 9 is an angled view of an oval expander according to another embodiment of the present disclosure.

FIGS. 10-11 are side and section views, respectively, of the oval expander shown in FIG. 9.

FIGS. 12-13 are side and section views, respectively, of a D-shaped expander according to another embodiment of the present disclosure.

DETAILED DESCRIPTION

The present disclosure is directed to structures, systems and methods for the creation and expansion of surgical portals in a body of a patient so that particular anatomy may be operated on, such as the spine. Because the expanders of the present application are used to expand retractor systems and assemblies initially inserted into the body, such retractors are made reference to throughout the application. The expansion concepts described herein will largely be discussed as expanding rods of retractors like the retraction mechanisms disclosed in the '228 Publication. However, it should be understood that the present application has applicability to retractors having more traditional blade structures. Indeed, the expander concepts employed to interact with the rods shown and discussed in the present application could be applied to bladed structures as well.

In one approach to access a surgical site, retractors inserted into a body of a patient are expanded to create a surgical portal to a surgical site using a method known as sequential dilation. Initially, a retractor with a plurality of rods or blades is inserted into the body of the patient. Then, a sequence of circular dilator elements are inserted in between the rods or blades to increase a volume encircling the rods or blades. In particular, these circular dilators are placed concentrically so that after a first dilator is placed, a second dilator is placed over the first one and so on. One example of this approach is described in U.S. Pat. No. 8,992,558, hereby incorporated by reference herein in its entirety.

Figure 1:
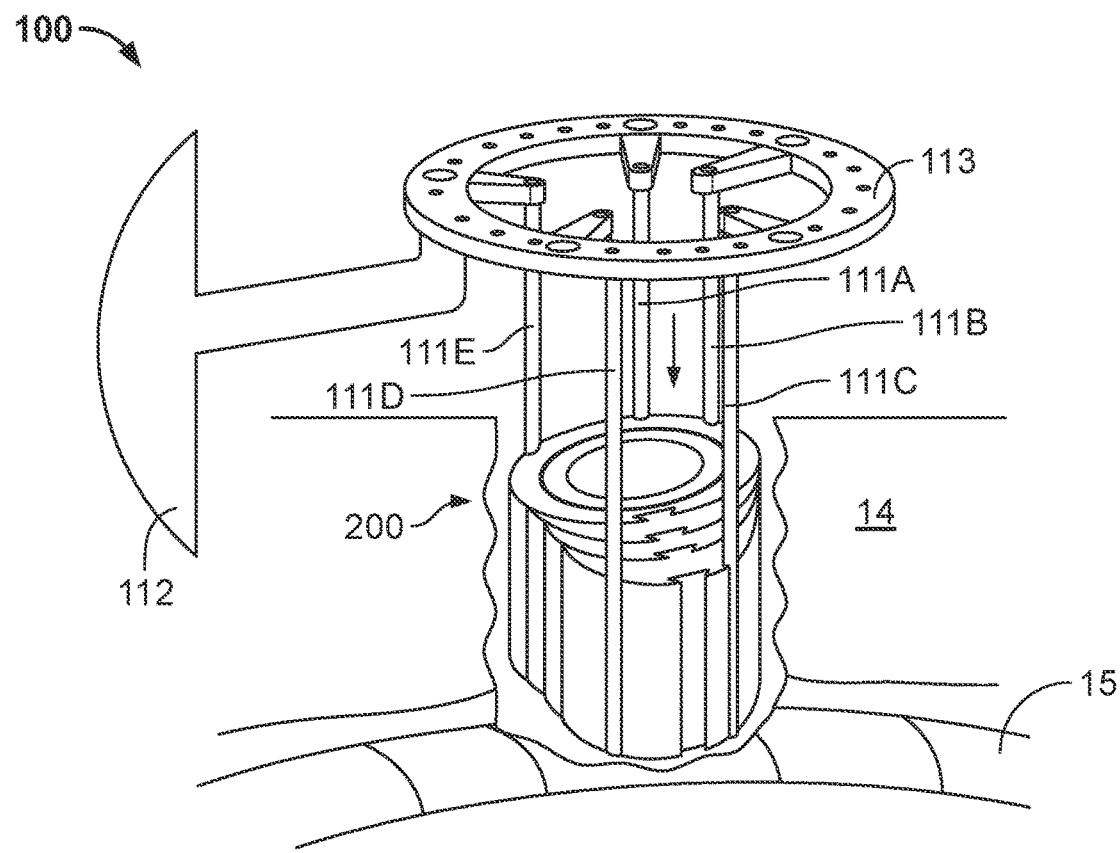
FIG. 1 is a perspective view of a retractor system with a series of expanders according to one embodiment of the present disclosure placed therein.
Figure 2:
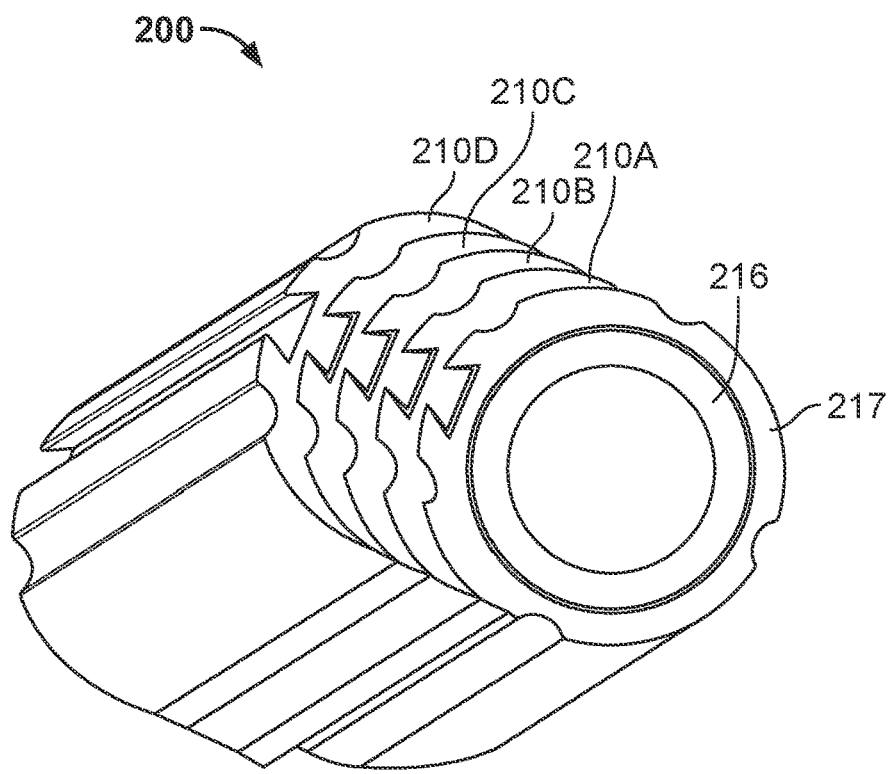
FIG. 2 is a close up view of an assembled expander set according to one embodiment of the present disclosure.

Unlike traditional approaches such as the one described immediately above, the present application provides structures, systems and methods for sequential expansion in a unilateral direction. Moreover, the expansion contemplated herein may also create non-circular surgical portal shapes, such as oblong, oval and D-shaped portals. This is advantageous in that it is often desirable to operate in a surgical space of these shapes compared with a circular or near circular opening. One example of an expander set of the present application sized to create an oblong portal is shown in FIGS. 1 and 2. FIG. 1 depicts a retractor system 100 with a frame 113 and rods 111A-E similar to that disclosed in the '228 Publication with an expander set 200 disposed therein. As is shown in FIG. 1, expander set 200 has distracted rods 111A-E to create an oblong portal within tissue 14. In the particular embodiment shown in FIG. 1, this retraction is accomplished through the use of the components of expander set 200, which is discussed more fully below along with many other embodiments.

Expander Set with Shims

Figure 3A:
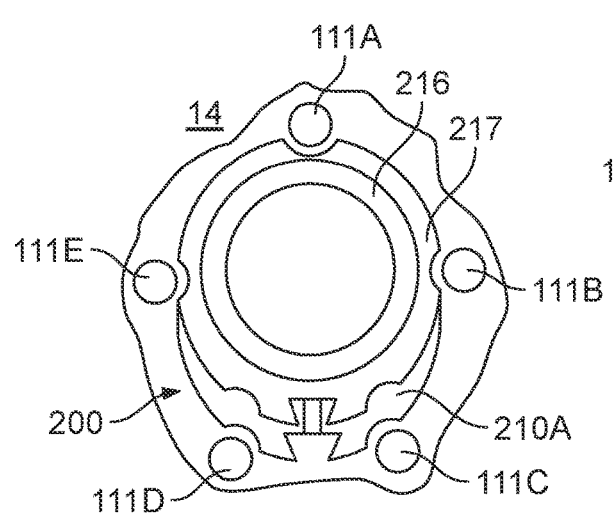
FIGS. 3A, 3B, 3C and 3D depict steps in a method of expanding a plurality of rods according to one embodiment of the present disclosure using components of an expander set.

In one embodiment, expander set 200, through its constituent components, is used to retract rods of a retractor 100 such as the plurality of rods 111A-E shown in FIG. 1. In some examples, such as is shown in FIG. 1, the rods are cylindrical in shape. Expander set 200 is shown in its fully assembled form in FIG. 2 while its components are shown individually in FIGS. 4-8. As shown, expander set 200 includes a tube or probe 216, a base expander 217, and a plurality of shims 210A-D. Expansion of a portal via expander set 200 is supplemented with the placement of a tissue retaining ring 218 over the tube combined with base expander and shims, as best shown in FIG. 3C.

Tube 216 is the innermost component of expander set 200, and is shown in FIGS. 2 and 3A-3C. As depicted, tube 216 has a cylindrical shape with a generally smooth outer surface. Although not shown in the figures, tube 216 may include a taper on one end (preferably a distal end) to improve the ease with which it may be inserted into a space between rods. Sized to fit over tube 216 is base expander 217, best shown in FIGS. 4 and 5. Base expander 217 has a length extending from a proximal end 201 to a distal end 202 and contains a smooth inner surface 205, and an outer surface with a plurality of curved grooves 203 and a shim groove 204, which in the depicted embodiment, takes the form of the female portion of a dovetail joint. Smooth inner surface 205 is dimensioned to correspond to an outer surface of tube 216 so that it fully encapsulates tube 216 when inserted thereon. Grooves 203A-E, 204 have a length extending between proximal end 201 and an interior location 206 near distal end 202. As depicted, the length of grooves 203A-E, 204 generally corresponds to a length of shims 210A-E. The outer surface of base expander 217 is tapered starting from interior location 206 to the distal end 202 to improve the safety and efficiency of an advancement of base expander 217 through the body of the patient. In this manner, the shape of base expander 217 allows for a smooth insertion and minimizes damage to surrounding tissue. As noted above, base expander 217 is designed to be placed over tube 216, thereby circumferentially enlarging the tissue portal.

Shim 210A is illustrated in FIGS. 6 and 7 and has a length that extends between proximal end 211 and distal end 212. Shim 210A includes two curved grooves 213A-B, a shim groove 214, a shim protrusion 215, a pair of and two shim protrusions 208A, B. Protrusions 208A,B are sized to correspond to grooves 203A, 203B while shim protrusion 215 (designed as the male portion of a dovetail joint) is sized to correspond to shim groove 204. In the embodiment depicted in FIG. 7, each of the groove and protrusion features extends over the length of shim 210A. These features allow shim 210A to releasably engage with base expander 217 in a secure manner. A cross-sectional shape of shim 210A is generally semicircular with a circumferential distance between end 207A and end 207B of a sufficient size to encompass a portion of the outer surface of base expander 217. As shown in FIG. 7, for example, a thickness of the cross-section of shim 210A tapers from a central location proximal to shim protrusion 215 to generally pointed tips at ends 207A-B. The respective shapes of base expander 217 and shim 210A are such that when combined, an oblong shape with rounded edges is defined, such as that shown in FIG. 3A.

The features on the outer surface of shim 210A are configured so that additional shims may be added over shim 210A while providing a smooth contact surface between tissue 14 and rods 111A-E, as will be described in greater detail below. Indeed, the further shims (see FIG. 3C) employ similar configurations, although they can exhibit different dimensions. In this regard, it is noted that differently sized shims may be provided thereby allowing for a particularly sized and shaped portal to be created in the body.

Tissue retaining ring 218, as shown in FIG. 8, is of an oblong cross-section sized to fit over expander set 200. An inner surface 225 of retaining ring 218 is generally smooth, but includes recesses 224 which provide extra space for tools to engage retaining ring 218 during insertion or other accessories, such as, an LED light or neuro-monitoring devices. At a distal end of tissue retaining ring 218 is a circumferential groove (not shown) with sufficient depth to place an additional ring (not shown) inside the retaining ring. Such ring could be a disposable LED ring, for example, so that greater visibility is possible at the surgical site. An outer surface of retaining ring 218 includes a plurality of curved grooves 223A-E sized to accommodate disposal of rods 111A-E of retractor system 100 therein, or other retractor systems, as applicable. In some examples, a shape of the grooves in the retaining ring and shims is such that rods disposed therein mate with the groove. In one example, the expander set includes components sized so that base expander 217 has an inner diameter of 16.5 mm and retaining ring 218 has a corresponding size. In this example, shim groove 204 can have a width varying from 2.6 mm to 4.5 mm, becoming wider toward the body of the shim, as seen in FIG. 5, for example.

Expander set 200 may be varied in many ways. For example, the tube may have a tapered end to allow for a smooth insertion and to minimize tissue damage. Further, the tube may include a plurality of curved grooves to securely engage the rods during insertion. In some examples, four, five or more shims may be incorporated as part of the expander set. In another example, the grooves on the base expander and the shims may be of a quantity that corresponds with any number of rods. Additionally, the grooves are not limited to being curved in shape and may be any shape corresponding to the rods. For example, the grooves may be rectilinear. Further, the shims may have greater or lesser thicknesses to allow for more or less precise expansion. Similarly, a thickness of the shims may vary from one shim to another in an expander set. Additionally, any two grooves may be of a different shape from each other where corresponding rods have different cross-sectional shapes. Similarly, the inner or outer surface of the base expander and the inner concave surface of the shims are not limited to being circular or round in shape, and may be any shape and in particular any clinically relevant shape. For instance, the base expander may be oval, oblong, rectangular, or triangular and the shims may have a shape corresponding to a portion of a perimeter of the base expander. Of course, the tissue retaining ring may be dimensioned to correspond to any shape created by the combination of the base expander and the shims secured thereto. A size of the expander set components can be made to correspond to applicable surgical needs. For example, when surgery involves placement of a plate, the tissue retaining ring may have an opening measuring 23 mm by 30 mm, whereas for surgery that involves a smaller implant, the tissue retaining ring may measure 6 mm by 22 mm. Of course, in the event a particular surgery requires another opening size, the elements can be sized accordingly. A thickness of the ring shaped expanders and the widest location on the shims may be as little as 1 mm. However, narrower thicknesses are also contemplated, particularly where the materials used make such materials a viable option. For example, it is contemplated that under same circumstances, a thickness of the retaining ring or base expander may be as little as 0.5 mm. An upper limit on the thickness of the expander elements is generally controlled by pragmatic considerations, such as whether the thickness is so large that it impedes access.

Further, additional surface features may be included on the proximal ends of the base expander and/or shims to improve engagement between those elements and an insertion tool. Additionally, indicating markers may be included along the length of the base expander and/or shims to allow for greater precision during the insertion. In still further examples, each of the base expander, shims and the retaining ring may have varying lengths relative to the rods and with respect to each other. In other examples, any number of the base expander and shims may comprise optically clear or translucent material to aid in visualization of the surgical site. One exemplary clear material is glass. Similarly, lighting features can be incorporated into one or more elements of the expander set. Lighting may be in the form of LEDs, with some examples capable of incorporation into the expanders of the present disclosure described in the application entitled "Bridges and Lighting for Lateral Access." The above features can also be included as a combination. Clear or transparent expanders, when combined with lighting, can significantly enhance visualization of anatomy within the patient.

The tissue retaining ring may be one solid structure or it may be a combination of elements i.e., composite structure. For example, the tissue retaining ring may be a combination of rigid and semi-flexible materials. Where the retaining ring has such a structure, surfaces of the tissue retaining ring that come into contact with rods will be rigid and components connecting the base expander and shims will be flexible. This allows for the possibility of more complex expansion shapes. The overall design may be manufactured out of a cost-effective but durable material such as aluminum, although any material suitable for use in the body is contemplated. The tissue retaining ring may also be configured to include lighting such as that described above to provide illumination to a surgical site.

In another aspect, expander set 200 is employed in a method of creating a tissue portal in a patient during a lateral spinal surgery. Although the embodiments herein are described in the context of lateral approaches to the spine, other approaches are also contemplated. These include, for example, anterior and posterior approaches. The choice of approach often depends on the type of implant being placed. For example, an anterior approach may be used for anterior lumbar interbody fusion implants. In addition to procedures involving the spine, the concepts described throughout the specification may also be employed outside of the spine. In this manner, where reference is made to fixation of a posterior rod, such fixation may be at another location with a different approach. For example, an anterior rod may be fixed and other rods may retract relative to the anterior rod. Returning to the methodology for creation of a portal in lateral spine surgery, such method will be discussed in connection with retractor system 100, although other retractors or the like may be employed.

In operation, expander set 200 unilaterally expands the tissue portal to the desired size allowing for the tissue portal to be a more clinically relevant shape when performing surgeries, thus minimizing tissue damage and removing unnecessary pressure on nerves and muscles. In one embodiment, with a guide wire and retractor already advanced into the patient at a desired location, a posterior rod is fixed in place in the body as expansion using shims occurs in an anterior direction. The posterior position for the rod is determined so that a nerve root is anterior to, and thus outside of, a path of expansion. With the rods in position, tube 216 is placed over the guide wire, thereby causing an initial expansion of rods 111A-E in multiple directions. Base expander 217 is then inserted over the tube 216, circumferentially expanding the retractor rods 111A-E and also the tissue portal in multiple directions. Advancement of base expander 217 is aided by the tapered shape proximal to distal end 202. During insertion, grooves 203A-E preferably engage rods 111A-E and maintain engagement once base expander 217 is fully advanced to the surgical site, thereby keeping rods 111A-E stable and minimizing their movement.

With base expander 217 in place between the plurality of rods 111A-E, shim 210A is inserted onto base expander 217. To engage shim 210A with base expander 217, protrusion 215 of shim 210A is inserted over shim groove 204 on base expander 217, as shown in FIG. 3A. When protrusion 215 is aligned with shim groove 204, protrusions 208A-B fit within and otherwise mate with grooves 203A-B. Shim 210A is then slid down base expander 217 until distal end 212 of shim 210A is positioned near location 206 on base expander 217. Insertion of shim 210A over base expander 217 as shown in FIG. 3A causes tissue portal (e.g., retraction of tissue 14 shown in FIG. 1) to unilaterally expand (for instance, only in an anterior direction). During insertion of shim 210A, rods 111C and 111D become disposed within grooves 213A, 213B and are unilaterally shifted in a direction away from tube 216. FIG. 3A illustrates the position of rods 111A-E when shim 210A is advanced over base expander 217.

Figure 3B:
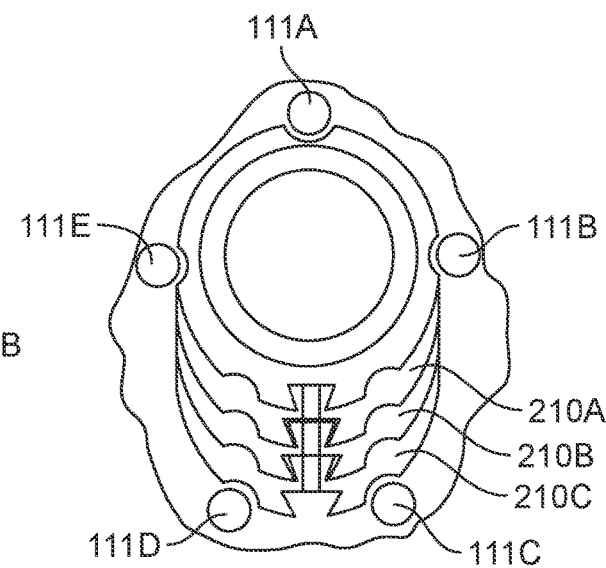
Figure 3C:
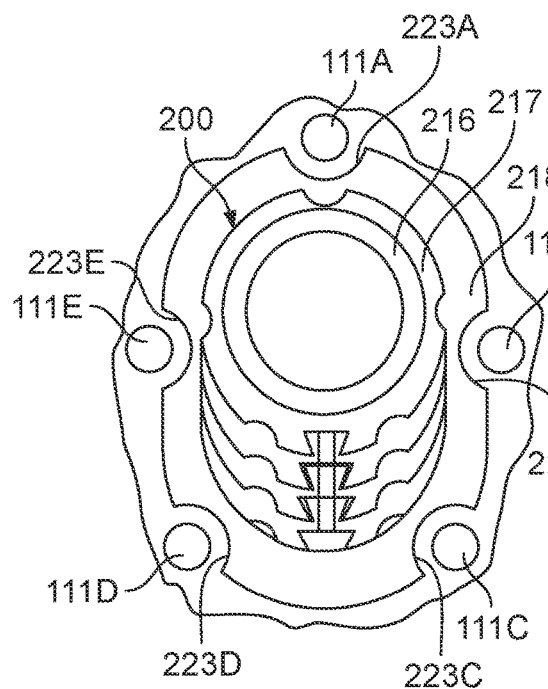

FIG. 3B shows additional shims 210B and 210C inserted over the initial shim 210A. Shims 210A, 210B, and 210C, as shown, are all the same size and shape. This configuration is achieved by first inserting shim 210B over shim 210A in the same manner as described above for shim 210A as it is inserted over base expander 217. This is repeated for shim 210C once shim 210B is in place. As shown comparing FIGS. 3A and 3B, each successive shim inserted onto the expansion set further retracts rods 111C, 111D unilaterally away from tube 216, thereby increasing the portal size, as well as defining it as more of an oblong shape. This individual shim insertion for incremental expansion of the rod structure may allow for safer creation of a surgical portal while still obtaining a desirable portal size following the insertions of the desired number of shims. Of course, additional shims may be added to obtain a desired portal size. For example, FIG. 2 shows an expansion set 200 with four shims 210A-D. It is also contemplated to provide and utilize differently shaped shims from those depicted as well as differently shaped shims within a particular expander set.

Figure 3D:
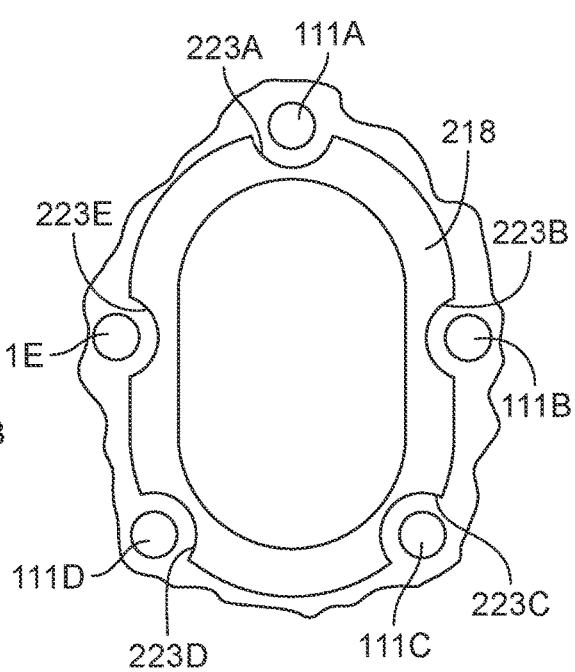

Once a desired tissue portal size is reached, tissue retaining ring 218 is inserted over expander set 200 (see FIG. 3C). In one example, as shown in FIG. 3C, an open space within tissue retaining ring 218 is filled by the expander set 200. As tissue retaining ring 218 is placed over expander set 200, grooves 223A-E engage with rods 111A-E to further expand and maintain the stability of rods 111A-E as tissue retaining ring 218 is advanced toward the surgical site. The expansion of rods 111A-E is in multiple directions with the advancement of retaining ring 218. Typically, tissue retaining ring 218 is advanced until it is proximal to distal ends of rods 111A-E. In this manner, once expander set 200 is removed, as shown in FIG. 3D, tissue retaining ring 218 continues to hold rods 111A-E in place and also prevents tissue creep into the portal. When tissue retaining ring 218 is at the distal ends of rods 111A-E, tissue creep is prevented close to the surgical site, where it is most important to maintain a clear working area for the surgeon. Tissue retaining ring is preferably left in place during the surgery to maintain a portal into the surgical site and to provide lighting, as applicable.

In a variant of this method, the combined base expander 217 and shims 210A-D are removed after each is fully advanced into the portal to expand its size. With all expanders removed, the retaining ring 218 is placed separately into the portal. This is typically done shortly after removing the base expander and shims. In this manner, a retaining ring having the same outer dimension as the base expander can be used for the same procedure, although this approach is not limited to such expander component sizes. The method may be performed with any combination of the alternative embodiments and examples as described above.

Oval Expander

In another embodiment an oval expander 300 can be provided to cause the expansion of the retractor (see FIGS. 9-11). Expander 300 has a length between a proximal end 301 and distal end 302, with the latter being configured to enter the body first. The oval cross sectional shape is best shown in FIG. 11 and, as opposed to expansion set 200, only a single structure is provided, although such structure may comprise composite materials. Expander 300 includes a taper extending from distal end 302 to a base 306. The tapering portion allows for a smooth insertion of expander 300 and minimizes tissue 14 tears or other tissue damage. Of course, while shown and discussed above as a single component structure it is contemplated that a plurality of nesting oval expanders can be provided and utilized like traditional sequential dilators.

Oval expander 300 includes a smooth oval shaped inner surface 305 while an outer surface contains a plurality of ribs 320 adjacent proximal end 301, each extending around a perimeter of oval expander 300. The plurality of retractor ribs 320 are preferably evenly spaced between proximal end 301 and partial depth location 321. These ribs may, for example, aid in providing grip for a user of the expander. The outer surface is an oval shape as well, with rounded ends 311A-B. The outer surface also includes indicator markers 319 positioned at various locations along the length of expander 300 so that a distance between the marker and distal end 302 may be identified. This can aid a surgeon in advancing the expander to a particular depth in the body of the patient. Yet another feature on the outer surface of oval expander 300 is a plurality of rod grooves 303 extending parallel to the length of the expander. The rod grooves 303 extend over a majority of the length of oval expander 300, as shown in FIGS. 9 and 10. Grooves 303 ensure the rods of the retractor remain stable from an early stage in advancement of the expander through the necessary retraction during the surgical procedure. The opening defined by inner surface 305 provides an option of inserting expander 300 over a guidewire or other probe. In this manner, oval expander 300 is designed to operate with a closed set of rods or a set partially distracted by an initial probe. In one example described in the '228 Publication, a probe is built into the assembly and enters the body with the rods. It is pulled out prior to additional distraction, creating a space to accommodate further expansion, such as expansion with oval expander 300.

A cross-sectional size of oval expander 300 is sufficiently small so that oval expander may be inserted into a retraction assembly having a plurality of rods in a closed position without any previous expansion mechanisms having been inserted therebetween. The shape of expander 300 provides an oval shaped portal when used to expand a retraction system.

FIGS. 12-13 depict another embodiment of a non-circular expander in the form of a D-shaped expander 400, which has a D-shaped cross-section. D-shaped expander 400 includes a smooth oval inner surface 405 similar to oval expander 300. However, instead of having two rounded outer edges 311A-B, D-shaped expander 400 has one rounded outer edge 411 with an opposing generally flat outer edge 413, as best shown in FIG. 13. D-shaped expander 400, as depicted in FIGS. 12 and 13, includes the same features on its outer surface and the same taper as oval expander 300. D-shaped expander 400 allows for the opening of retractor rods to a D shape, thereby forming a D-shaped portal in the body of the patient.

The oval and D-shaped expanders may be varied in many ways. For example, the expanders may include any number of oblong or polygonal shapes for the outer and inner surfaces (e.g., square, rectangular, etc. . . . ), which can provide tissue portals with such shapes. Further, the oval and D-shaped expanders may include only one of the rib and indicator marker feature, or neither. The taper may be longer or shorter proportional to the length of the expander than that shown in FIGS. 9, 10 and 12. The cross section at the distal tip in the tapering portion may also be of a different cross-section than that of the main body of the expander (e.g., circular). Similarly, the oval and D-shaped expanders may have a cross section that tapers over the entire length. As with the expander set described above, the grooves may be any sectional shape as a matter of design choice to accommodate the shapes and sizes of rods to be engaged for expansion. Additionally, the expanders may have any number of grooves thereon.

Figure 14:
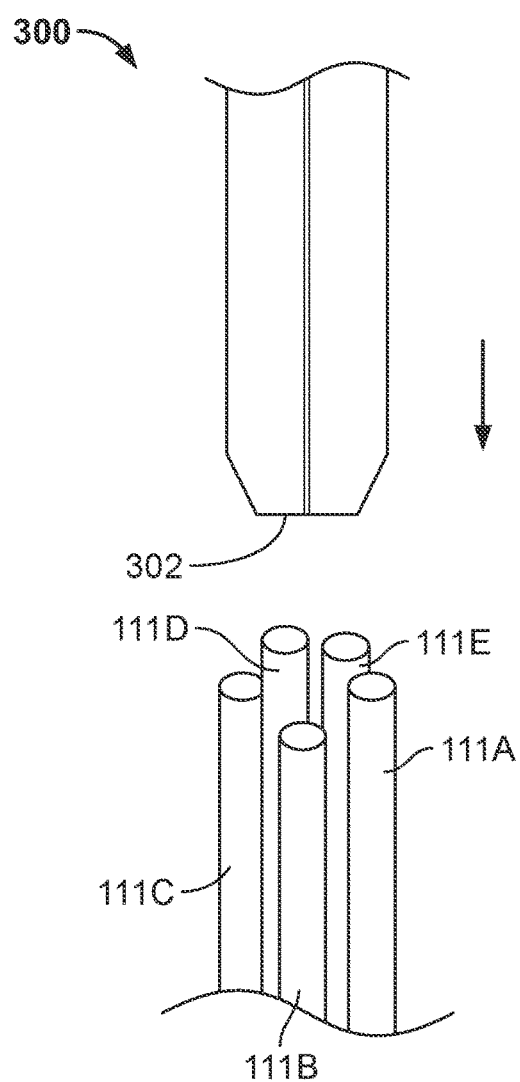
FIGS. 14-15 illustrate steps in a method of advancing the oblong expander of FIG. 9 into rods of a retractor.
Figure 15:
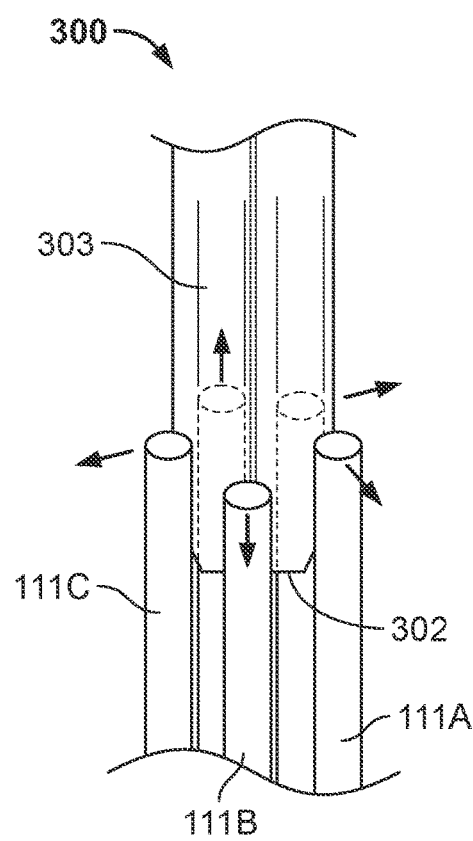

FIGS. 14 and 15 depict the use of expander 300. In FIG. 14, the expander is being prepared for insertion between a set of rods 111A-E. As expander 300 is advanced, as shown in FIG. 15, rods 111A-E are displaced so that a space in between them is enlarged and takes the general shape of the cross-section of the expander. During this expansion, rods 111A-E preferably remain within grooves 303 so as to maintain the smooth expansion of the device. While expander 300 preferably results in an oval opening between rods 111A-E, the similar use of D-shaped expander 400 will preferably result in a D-shaped opening. Once oval expander 300 or D-shaped expander 400 have been fully inserted, a retaining ring similar to ring 218 that cooperates with the particular expander can be inserted to maintain the portal size upon removal of the expander.

Spring Expander

Figure 16:
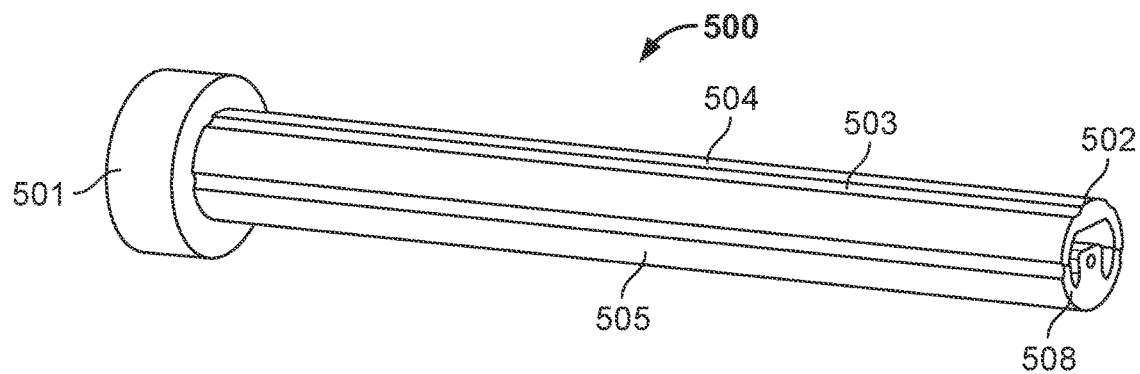
FIG. 16 is a perspective view of a spring expander according to another embodiment of the present disclosure.

FIGS. 16-19B depict yet another embodiment of the expander. In particular, a spring expander 500 having a length between a knob 501 and a distal end 502 is shown in those figures. Knob 501 is connected to a central member 510 that extends along the length of spring expander 500. Central member 510 is positioned within a central core region 511 of spring expander 500 between an upper portion 504 and a lower portion 505, and is described in greater detail below. Both upper portion 504 and lower portion 505 include grooves 503 as shown in FIG. 16, which allow for controlled engagement between the rods of a retractor system and spring expander 500 when spring expander 500 is placed through the rods of the retractor system. The various components of spring expander 500 as described are best shown in the exploded view of FIG. 19B.

Figure 17:
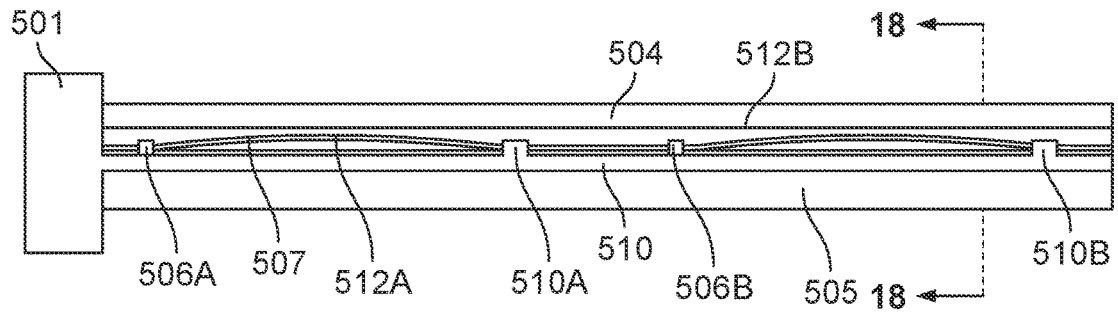
FIGS. 17-18 are side and sectional views, respectively, of the spring expander of FIG. 16 in the closed position.
Figure 18:
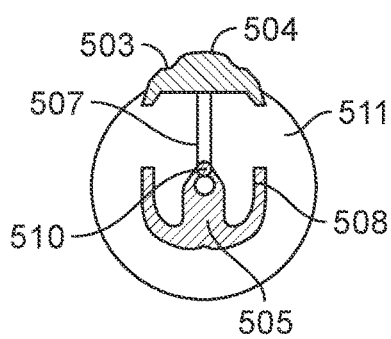
Figure 19A:
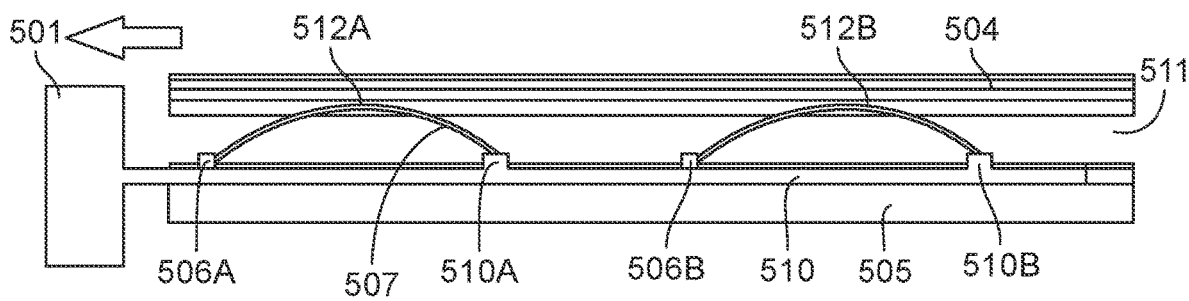
FIG. 19A is a side view of the spring expander of FIG. 16 in the open position.
Figure 19B:
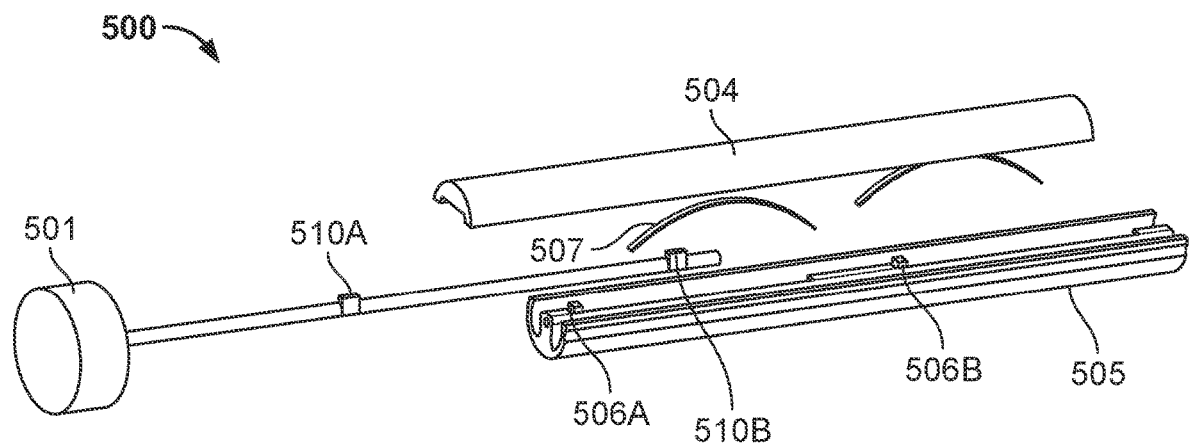
FIG. 19B is an exploded view of the spring expander of FIG. 16.

Central member 510 further includes springs 507 secured thereto, as shown in FIGS. 17, 19A and 19B. In particular, springs 507 are secured to central member 510 at two locations on the length of central member 510 and are also connected to lower portion 505 at two locations. In the depicted embodiment, a first spring is attached at block 506A on lower portion 505 at one end and at block 510A on central member 510 at another end. The spring is also connected to upper portion 504 at a midpoint attachment 512A between blocks 506A and 510A. Similarly, a second spring is connected to block 506B at one end and block 510B at another end. As depicted, each spring is connected to the lower portion so that both respond to a single actuation, for example, a pulling of knob 501. In a variant, a single spring may also be used. Blocks 506A and 506B are connected to central member 510 while blocks 510A and 510B are connected to lower portion 505. As best shown in FIGS. 17 and 19A, blocks 510A-B are configured to move in response to pulling of knob 501, with such movement causing springs 507 to bend, as respective blocks at the ends of each spring become closer together. To this end, as will be described further below, the springs are configured to bend outward toward the core region between upper and lower portions 504, 505 of spring expander 500 in response to pulling of knob 501. In one example, the upper and lower portions of the spring expander each have a surface with a radius of 10 mm so that spring expander has an outer radius of approximately 10 mm in the closed position. The Knob for this expander moves up to 10 mm when actuated between a position abutting the upper and lower portions and a fully withdrawn positon.

The spring expander may be varied in many ways. For example, it may include any number of springs along with a requisite number of corresponding blocks to secure the springs. Additionally, multiple knobs may be embedded within one other, each corresponding to a respective core member and spring. In this manner, knobs may be pulled in sequence one after the other to cause a tissue portal to be opened in a cascading fashion. Such configurations may also be used to create openings with "toe-in" or "toe-out" effects at the distal end close to the surgical site. In other examples, different combinations of securement points (e.g., locations of the blocks as described above) may be used to secure springs to the spring expander, for example the blocks do not have to be equally spaced apart. Although the springs are shown as bands in the depicted embodiment, the spring or springs may be any spring known to those of skill in the art that will expand laterally in response to tension in a longitudinal direction. Additionally, the spring expander may have any number of grooves thereon.

Spring expander 500 is also preferably used in a method of expanding structures such as the retractor system shown in FIG. 1. Prior to use of spring expander in the method, a guidewire is typically in place through the body along with rods of a retractor. Additionally, an initial round expander (not shown) is placed between the rods for an initial expansion, although this is not required. In spinal surgeries performed using a lateral approach, initial insertion of the rods is performed so that one rod is positioned as a posterior rod and is fixed in one position. When the spring expander is actuated, as described below, it is understood that it expands a portal in an anterior direction away from the posterior rod. Of course, this is but one use for the spring expander.

Spring expander 500 has a closed position as shown in FIG. 17, in which core region 511 provides sufficient open volume so that blocks 506A-B, 510A-B and springs 507 do not apply measurable pressure onto upper portion 504. Core region in a partially closed position may be seen in the section view shown in FIG. 18, where it is apparent that there is space between upper portion 504 and lower portion 505. While spring expander 500 is in the closed position, it is advanced over the guidewire or initial expander in between the rods To expand spring expander 500, knob 501 is pulled in the proximal direction as shown in FIG. 19A. As knob 501 retracts in the proximal direction, core member 510 retracts in a corresponding fashion along with blocks 510A and 510B. During this time, lower portion 505 and blocks 506A, 506B will remain stationary. The pulling of knob 501 causes springs 507 to expand upward into core region 511, thereby pushing upper portion 504 away from lower portion 505 in a transverse direction as pressure is applied via the respective midpoint attachments 512A-B. Pulling knob 501 allows for incremental expansion of the rod structure, thus allowing for safer creation of a surgical portal while still obtaining a desirable portal size. A fully expanded spring expander 500 is shown in FIG. 19A, in which it can be appreciated that expansion effectively occurs in a single direction. Thus, the resultant expansion of the rods will largely be in that direction. Upon reaching a desired expansion, spring expander 500 is removed and a tissue retaining ring or another similar structure may be inserted into the portal to maintain its shape, in a similar fashion as described above. To contract spring expander 500 and return it to its closed position, knob 501 is pushed instead of pulled. In this process, the springs extend in length as they compress bringing upper portion 504 closer to lower portion 505. As this occurs, a distance between block 506A and block 510A becomes longer.

The springs utilized in this embodiment, like the other components of the present disclosure, may be made of any metal material suitable for use in the body of a patient, but should be sufficiently flexible and strong enough to withstand resistance from the forces required to displace tissue in the body. One advantage of spring expander 500 is that it allows for the unilateral expansion of a tissue portal with a single instrument, thus minimizing the number of tools needed for surgery. Additionally, expansion occurs away from the nerve root in spinal surgeries, thereby reducing the risk of injury. Similar principles may be applied to direct expansion in other surgical procedures.

Mechanical Expander

In yet another embodiment of the present disclosure a mechanical expander 600 is depicted in FIGS. 20-25. As shown, mechanical expander 600 includes a handle 609, a central core member 620 with an upper portion 620A and a lower portion 620B, arms 606, and a plurality of channel members 603. Handle 609 is configured to actuate central core member 620 to reduce or increase a length of central core member 620. The means of actuation may be any known to those of skill in the art. For example, the handle may operate as a piston to pull or push lower portion 620B relative to upper portion 620A. In another example, handle rotates to move upper portion 620A relative to lower portion 620B by means of an internal threading on corresponding portions of each element.

Figure 20:
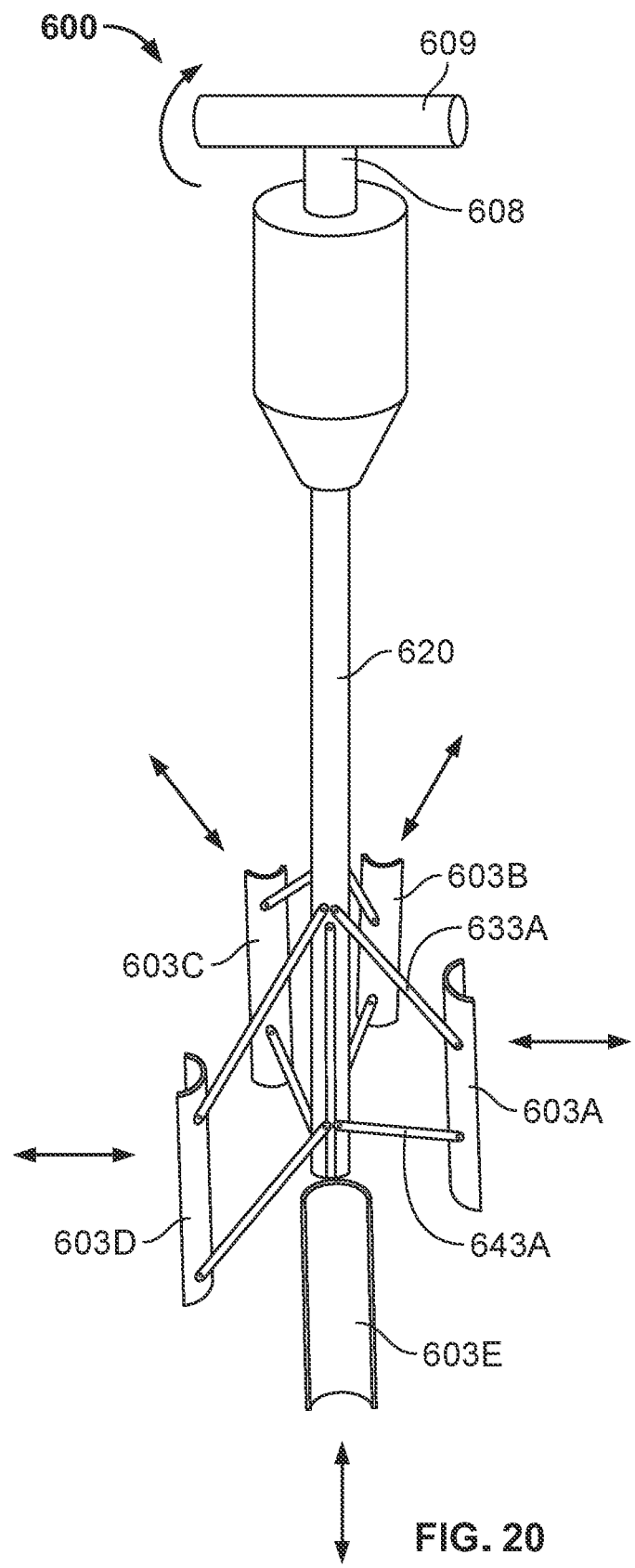
FIG. 20 is a perspective view of a mechanical expander according to another embodiment of the present disclosure.
Figure 21:
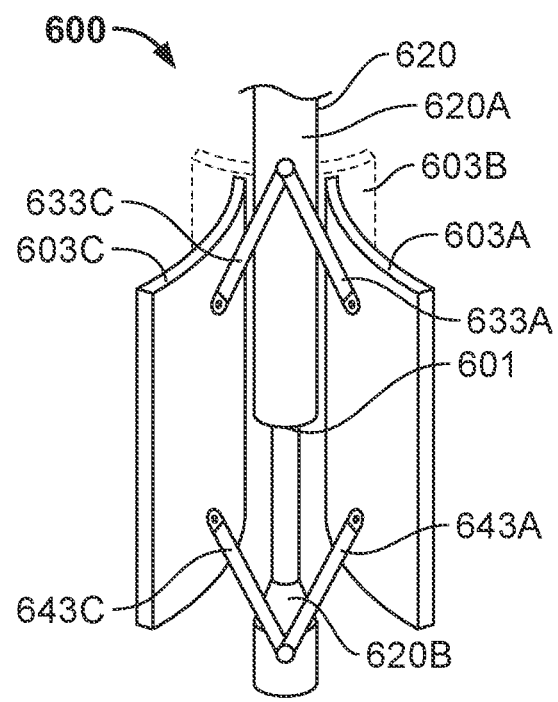
FIGS. 21-22 are close up views of a portion of the mechanical expander of FIG. 20 in the closed and open positions, respectively.
Figure 22:
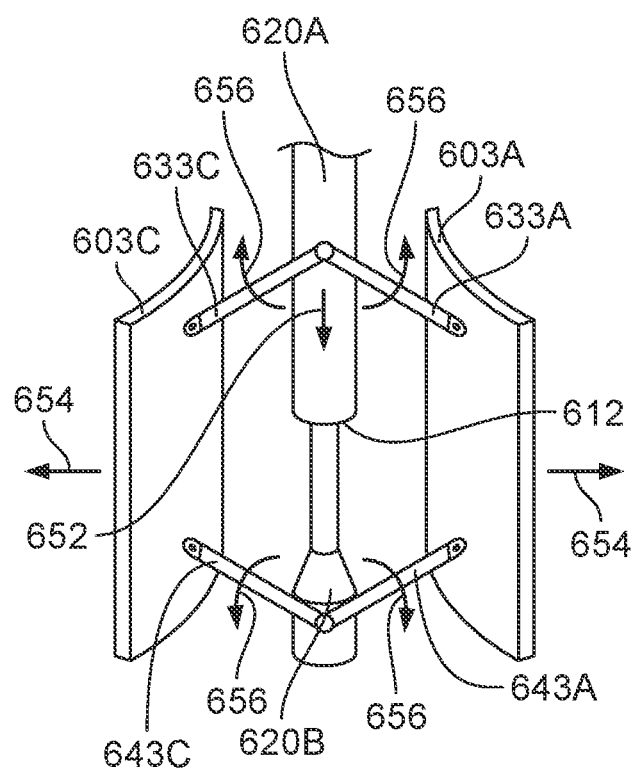
Figure 23:
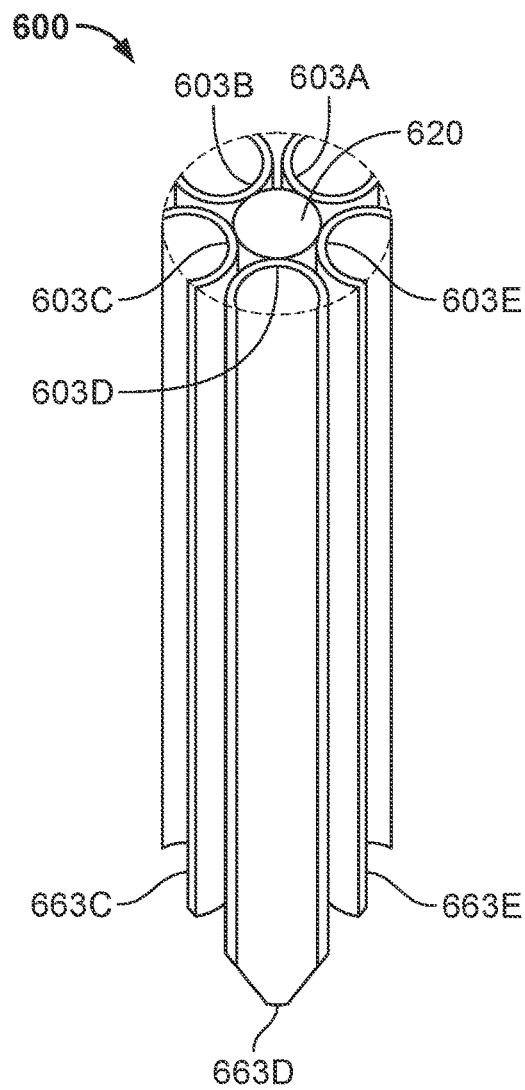
FIGS. 23-24 are close up perspective views of a portion of the mechanical expander of FIG. 20.

As shown in FIGS. 20-22, the plurality of channel members 603A-E are attached to both upper portion 620A and lower portion 620B of the central core member via arms 606. Channel members 603A-E are sized to engage with and otherwise support rods (not shown) when the mechanical expander is inserted over a plurality of rods. As shown in FIG. 23, channel members 603 include tapered lower ends (663C, D and E are shown) so that when mechanical expander is in a closed position, a distal end penetrating tissue provides for gradual expansion. The shape of this tip can vary in the closed position and may be closer to being flat in same variations.

FIG. 21 shows channel members 603 attached to the central core member. Each channel member 603A-E is connected to two arms including an upper arm 633A-E and a lower arm 643 A-E. For example, channel member 603A is connected to central core member via arms 633A and 643A. Upper arm 633A is connected to upper portion 620A of the central core member at one end and channel member 603A at another end, both via a hinged connection, as shown in FIGS. 21-22. Similarly, lower arm 643A is connected to channel member 603A at one end and lower portion 620B of central core member at another end, where each connection is hinged. In the embodiment as depicted, pairs of arms are similarly connected for each of the other channel members 603B-E, as best shown in FIG. 20.

In a closed position of the mechanical expander, as shown in FIG. 21, the hinge locations for each upper arm are positioned so that the connection to the upper portion of the central core member is closer to the handle than the connection to the channel member while the connection of the lower arms to the lower portion of the central core member is further from the handle than the connection to the channel member. This allows the arms to extend outward and away from the central core member when the mechanical expander is actuated, as described in greater detail below. In particular, the hinges allow the arms to rotate away from the central core member starting from a position where the arms are approximately parallel to the central core member and rotating outward to a desired amount. For example, the arms may rotate about the central core member such that each arm is perpendicular to the central core member.

Figure 25:
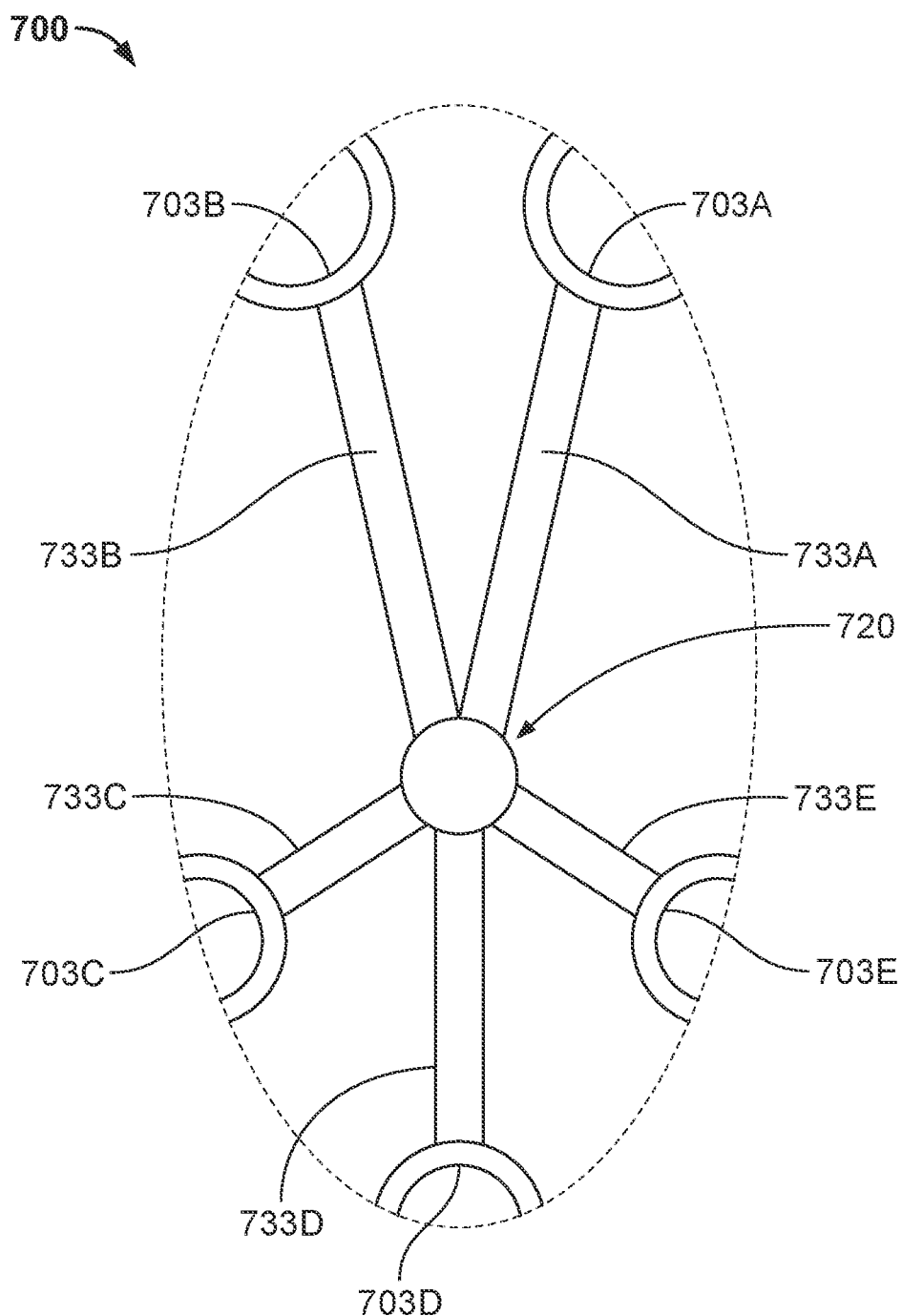
FIG. 25 is a top sectional view of a mechanical expander according to another embodiment of the disclosure.

The structure of the mechanical expander may be varied in many ways. For example, FIG. 25 depicts a mechanical expander 700 with arms 733A-E having varying lengths so that upon expansion, an oblong cross section is created. In particular, arms 733A-B are longer than arms 733C-E, so that as arms rotate about central core member 720, channel members 703A-B extend proportionately further away from central core member 720 than channel members 703C-E. In other respects, mechanical expander 700 is the same as mechanical expander 600 and like reference numerals refer to like elements. Mechanical expander 700 is shown in an open position in FIG. 25 to emphasize how arms of different lengths may be used to create non-circular shaped openings. This approach of varying arm lengths of the mechanical expander may be applied in any number of ways to suit desired portal opening shapes. Once a desired portal size has been reached, a retaining ring similar to that described above may be used to maintain the portal size upon removal of the expander. Depending on the exact dimensions of the arms, slots may be included in the central core member to accommodate arm movement. In other examples, the central core member and the channel members are connected by any means that allow channel members to move relative to central core member in response to actuation of the handle or other mechanism. For example, links, gears or balloons may be used in place of the arms. One way gears could be used involves actuation of the handle turning a gear structure connecting the channel members to the channel core. Balloons can be used in place of the arms to allow for more precise expansion by making incremental increases in balloon volume with an inert gas which pushes against the channel members.

In other examples, the number of channel members may be varied to correspond to the number of rods in a retractor. Thus, if there are six rods, then the mechanical expander would have six channel members. In still other examples, the handle and corresponding actuation mechanism may be varied using any means known to those of skill in the art. In one way, the components of the central core member may be configured so that pulling of the handle causes upper and lower portions to move closer together. For example, the arms are angled inward in a manner opposite to that shown in FIGS. 20-22 so that pulling upper portion away from lower portion causes channel members to expand outward in a lateral direction. In another example, a mechanism other than a handle may be used to actuate central core member, such as a button controlling pressure within the core member to change its length.

Additionally, another example includes multiple central core members, each attached to an individual channel member by dedicated arms. In this manner, expansion may be tailored to specific directions through the actuation of at least one central core member but fewer than all of the central core members. For example, if the mechanical expander includes five central core members, the actuation of one of those five, such as by means of a knob or handle attached to the respective central core member, would cause the portal to expand laterally in only the direction of expansion of the single channel member associated with that central core member. Such an expander would assist in minimizing the tissue damage caused by an unnecessarily large tissue portal and the possibility of unnecessary nerve compression.

In one embodiment of a method aspect of using a mechanical expander, the mechanical expander as shown in FIG. 20 is first retrieved and confirmed to be in the closed position, as shown in FIG. 21. If necessary, handle 609 is pulled to ensure the expander is closed, in the event that the arms are angled outward. Once in the closed position, i.e., where arms are approximately parallel to the central core member, as shown in FIGS. 21 and 23, the mechanical expander is then ready for insertion into a surgical site.

Figure 24:
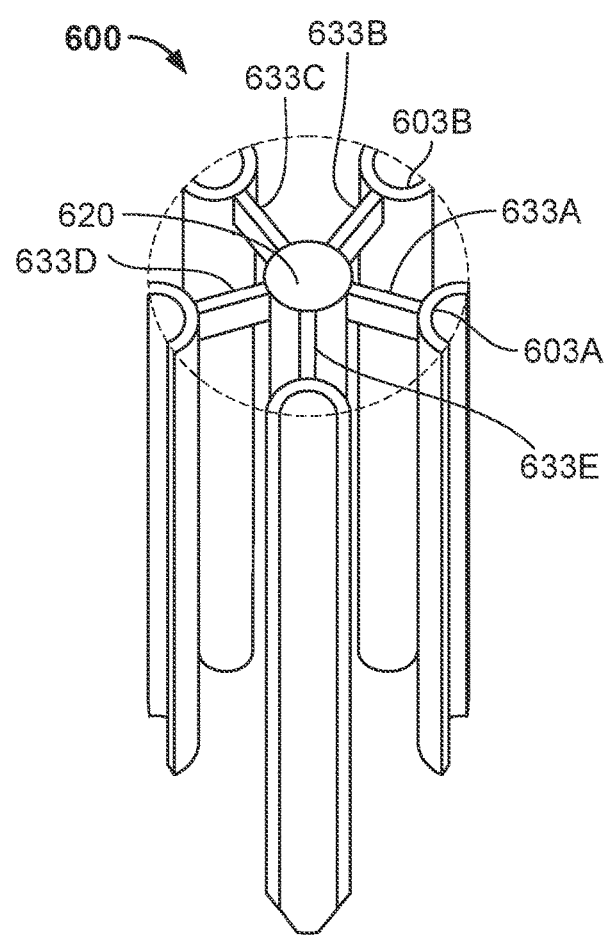

Mechanical expander 600 is then inserted through an opening in the rods of the retractor system. The mechanical expander is advanced to an extent deemed appropriate by the surgeon for the purposes of positioning the expander for expansion. For example, where the channel members have a length close to that of the rods, the mechanical expander is advanced to approximately the same extent as the rods in position within the body. In other examples, the mechanical expander may be advanced to a lesser extent. When mechanical expander is in its intended position between the rods within the body, handle 609 is then actuated to cause channel members to extend outward laterally from the central core member. This process is shown in FIG. 22. Actuation of the channel members by means of handle 609 allows for incremental expansion of the rod structure, thus allowing for safer creation of a surgical portal while still obtaining a desirable portal size and shape, e.g., oval shape, following the completion of the arm rotation. The upper portion 620A moves toward 652 lower portion 620B of the central core member. At this time, each of arms 633A-E, 643A-E rotate 656 about the central core member, pushing channel members 603A-E outward 654 as shown in FIG. 22 until a desired portal size is reached. FIG. 24 illustrates an expansion where the arms extend to an orientation nearly orthogonal to the central core member when handle 609 has been actuated to move upper portion 620A toward lower portion 620B of central core member. (To accentuate other elements of the expander, arms 643A-E are not shown in FIG. 24). During actuation as the channel members move laterally outward from the central core member, a shape of an inner surface of each channel member retains the respective rod therein so that the rod remains secured to the channel member during the expansion process. Once retraction using mechanical expander 600 is complete, the expander is removed from the body of the patient and the retracted surgical portal remains. Other preparatory procedures may be implemented at this time such as the insertion of a ring to hold the rods in position, but the choice of such procedures and whether to implement them is determined based on considerations such as the retractor structure used and the surgery being performed, among others.

In one example of a variant, the arms and the channel members may be configured so that the channel members are slanted or tapered in a distal direction toward the surgical site during use. This may ease insertion and provide a "toe in" portal where deemed advantageous. In this manner, the direction of expansion for each member may be changed according to surgical necessity.

Sleeve Assisted Expander

Figure 26:
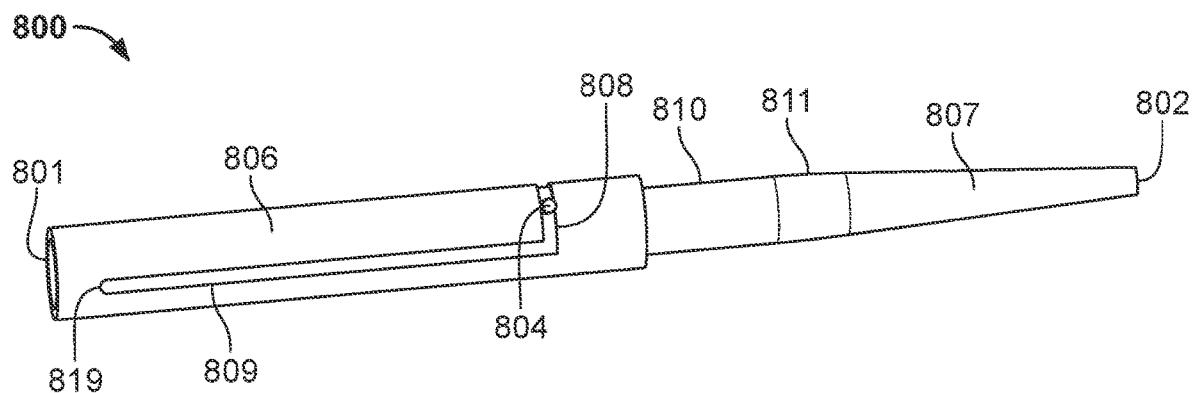
FIGS. 26-27 are perspective views of a sleeve assisted expander according to another embodiment of the present disclosure in a position prior to actuation and in an actuated position, respectively.
Figure 27:
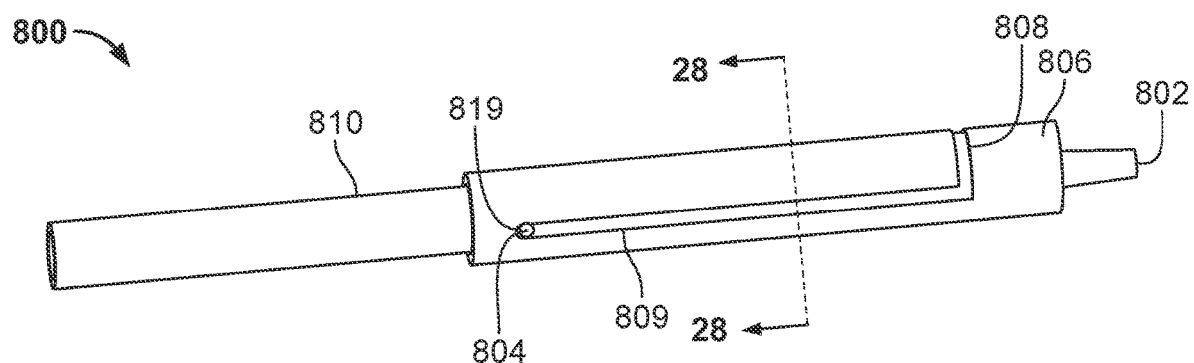
Figure 28:
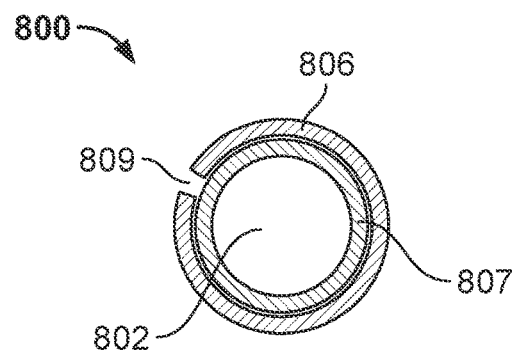
FIG. 28 is a sectional view of the sleeve assisted expander of FIG. 26.

Another embodiment of the present disclosure is directed to a sleeve assisted expander, as shown in FIGS. 26-28. Sleeve assisted expander 800 includes a body 810 with a length between a proximal end 801 and a distal end 802 and a sleeve 806 disposed thereon. On a surface of body 810 is a protruding stop element 804. Body 810 has a proximal portion with a generally smooth and cylindrical outer surface and a tapered portion 807 between a taper base 811 and distal end 802. Tapered portion 807 faces distal end 802 so that the sleeve assisted expander may be inserted into tissue with less resistance and the risk of damage to tissue, or other internal organs is minimized.

Sleeve 806 encapsulates body 810 over a portion of its length and includes a slot with a longitudinal portion 809 in communication with a transverse portion 808. In this manner, the combined slots 808, 809 form an L shape as seen in FIGS. 26 and 27. Slots 808, 809 have a width sufficient so that stop element 804 fits therein. Sleeve 806 is configured to move relative to body 810, and in any position of sleeve 806 on body 810, stop element 804 is positioned within one of slots 808 and 809.

The sleeve assisted expander may be varied in many ways. For example, the sleeve assisted expander may include a non-circular body such as an oval, rectangular, or other oblong shaped cross-section. In any one of these examples, the taper extending from the body portion may include the same type of cross section or the cross section may vary in the taper relative to the body portion. Additionally, the taper itself may be longer proportionally to the length of the expander. Similarly, the sleeve may have a cross-sectional shape corresponding to the body. In still further examples, the sleeve may be one type of shape and the body another. For example, the body may have a circular cross-section while the sleeve has an oval cross-section. In yet another example, the sleeve may include any number of grooves, slots or other recessed surfaces for receiving rods. In any one of the above examples, the sleeve assisted expander may include any number of sleeves, for example three sleeves with each one at least partially encapsulating the other or itself encapsulated. In another example, sleeves may be placed adjacent to one another along the length of the sleeve assisted expander. In yet another example, a rubber ring or washer can be included at an end of the sleeve facing the tapered portion of the body. This ring, connected at the end of the sleeve, expands or contracts to maintain contact with the surface of the body as the sleeve moves over the tapered portion of the body. In this manner, the rubber ring prevents tissue from getting caught between the sleeve and the body regardless of the position of the sleeve on the body. Of course, these principles can be applied to any number of expanders described throughout the application.

Figure 37A:
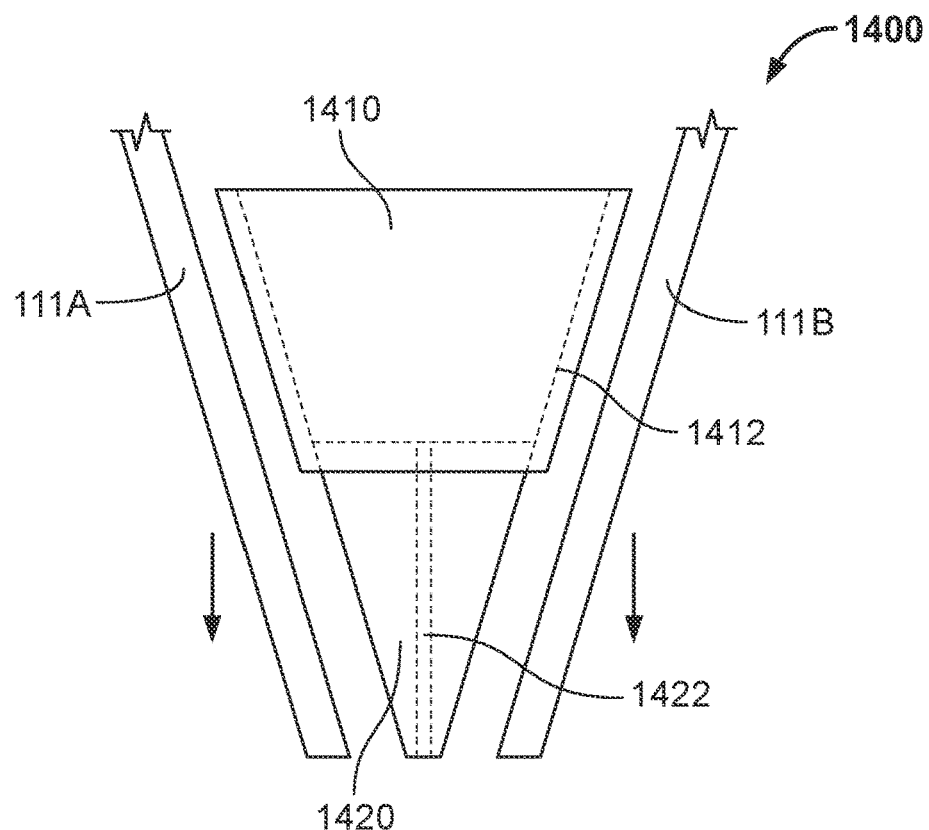
FIGS. 37A-B are side views of a telescoping expander according to one embodiment of the present disclosure.
Figure 37B:
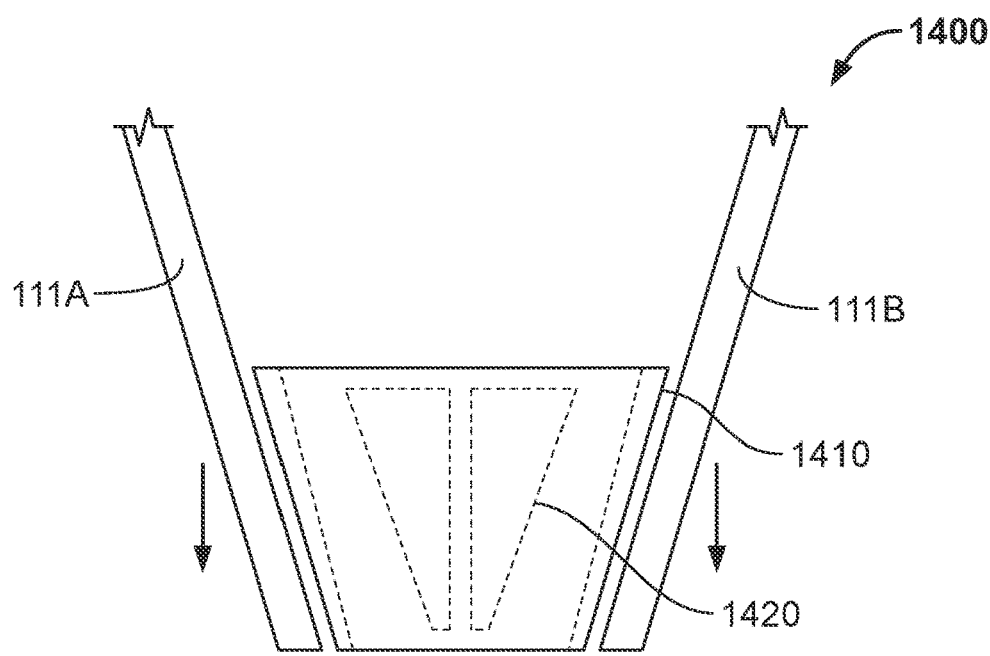

In yet another example, a telescoping expander with an active form of retraction is provided as shown in FIGS. 37A-B. As best shown in FIG. 37A, telescoping expander 1400 includes a sleeve 1410 and an inner body 1420. The sleeve has walls 1412 defining an opening sized to pass over inner body 1420. Both sleeve 1410 and body 1420 are tapered, as shown. Also, inner body 1420 includes an aperture 1422 therethrough sized to accommodate passage of k-wire, lighting or other small structures extant within the surgical portal. Sleeve 1410 and body 1420 are connected but are also movable with respect to each other, as described below. These principles of a telescoping expander can be applied to any number of sleeve components and using many different shapes, such as those described throughout the application.

As with the above expanders, the sleeve assisted expander is used in a method of retracting rods in a retraction system. While sleeve assisted expander 800 is in an unactuated position as shown in FIG. 26, stop element 804 is positioned within transverse slot 808 so that sleeve does not move relative to body 810. It is in this position that sleeve assisted expander is inserted into the body of a patient to reach a surgical site. As with the other embodiments already described, the rods of a retractor system are initially positioned and advanced into the surgical site and retracted as applicable prior to inserting sleeve assisted expander 800. Once ready, sleeve assisted expander 800 is advanced in between rods of the retraction system already in the body. Entry is eased due to the tapered portion 807 being the first to enter and causing the initial expansion. Once expander 800 is fully advanced so that distal tip 802 is proximal to the surgical site, sleeve may be rotated from proximal end 801 so that stop element 804 moves from transverse slot 808 to longitudinal slot 809. At this juncture, sleeve 806 is pushed axially toward distal end 802 and slot 809 slides over stop element 804 until stop 804 reaches an end 819 of longitudinal slot 809, as shown in FIG. 27. As sleeve 806 is advanced, the larger cross-section of the sleeve over body 810 further retracts the rods. This allows for incremental expansion of the rod structure, thus providing safer creation of a surgical portal while still obtaining a desirable portal size following the completion of sleeve advancement. Once a desired portal size has been reached, a retaining ring similar to that described above may be used to maintain the portal size upon removal of the expander.

In a method of using telescoping expander 1400, the expander is first inserted into the portal with the sleeve withdrawn from the body as shown in FIG. 37A. When a distal end of body 1420 reaches an intended destination within the portal, it remains in that position while sleeve 1410 can continue to advance over inner body 1420 and further into the portal. FIG. 37B shows how sleeve 1410 advances over body 1420, and in so doing, the portal size is further increased.

Wedge Expander

Figure 29:
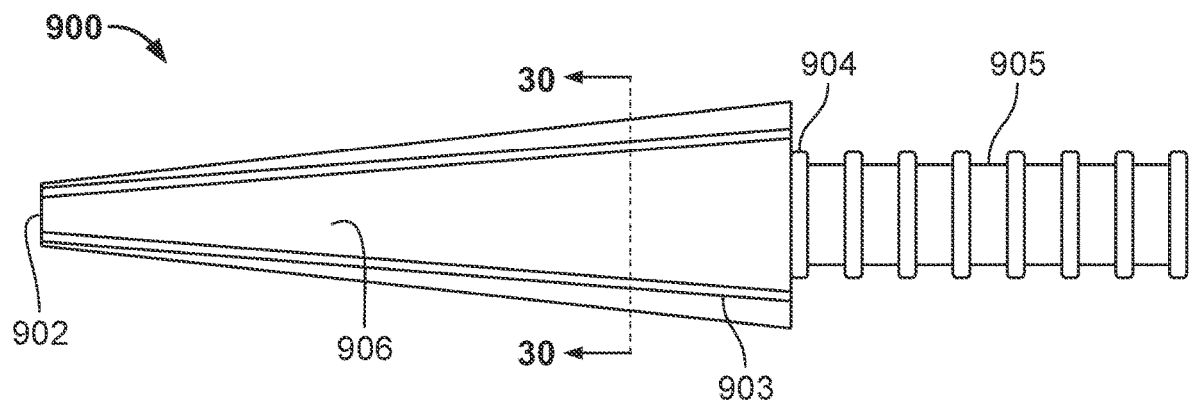
FIGS. 29 and 30 are perspective and sectional views, respectively, of a wedge expander according to another embodiment of the present disclosure.
Figure 30:
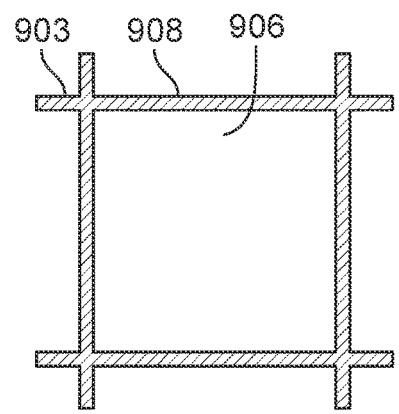

Another embodiment of the present disclosure is a wedge expander 900, as depicted in FIGS. 29-30. Wedge expander 900 includes a wedge portion 906 and a handle 905 including plurality of ribs. Wedge portion 906 has a truncated pyramidal shape tapering to a tip 902 and includes two ridges 903 extending from each edge of its cross-section, as best shown in FIG. 30. As evident from FIG. 30, each ridge 903 at any given edge is perpendicular to the other, creating a channel therebetween. The plurality of ridges 903 are configured so that rods may be slid between two ridges 903 at a single corner or between pairs of ridges at opposite corners in a channel 908 defined between ridge pairs 903. In this manner, ridges are configured to control movement of the rods as wedge expander is advanced through rods of a retractor in a more precise fashion while decreasing the steps required during the surgery. Handle 905 also includes a plurality of ribs as shown in FIG. 29 to assist with holding wedge expander 900.

In variations of the wedge expander, the wedge portion may include fewer than or greater than four sides. For example, the wedge portion may include three sides or five sides. In other examples, the ridges may be curved or any other shape extending from the wedge edge. Additional ridges may also be included on side surfaces of the wedge portion, particularly where the applicable retraction system includes a large number of rods. The cross-section of the wedge portion may be circular, ovular, other non-circular rounded shapes or any polygonal shape. In this manner, the wedge expander may be configured to create any number of surgical portal shapes. The tip of the wedge expander may be round, pointed or other shapes. The wedge portion may taper in an even fashion or may be jagged. In other examples, the wedge expander may include indication markers drawn along the side of wedge to allow for greater precision during advancement.

Figure 31:
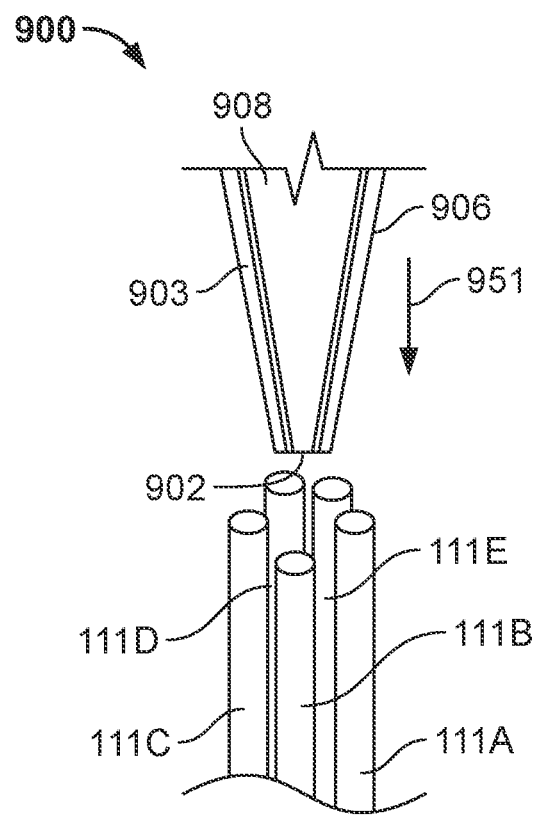
FIGS. 31 and 32 are steps in a method of advancing the truncated pyramidal expander of FIG. 29.
Figure 32:
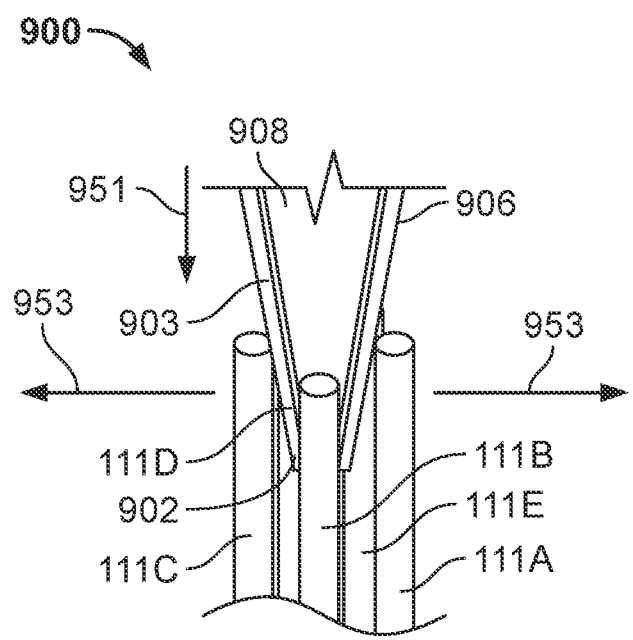

In a method of using wedge expander 900, a surgical site is first prepared by positioning and advancing a plurality of retractor rods 111A-E in a closed position into the surgical site to prepare an initial portal through the body. Wedge expander 900 is then inserted 951 in between the rods as shown in FIG. 31 and then advanced into the body in between the rods, as shown in FIG. 32. In the method as depicted, rods contact channel surfaces 908 as the wedge expander advances over the rods, which may control expansion of the rods as the rods are contained within ridges 903. The pyramidal shape of wedge portion 906 allows for incremental expansion of the rod structure, thus allowing for safer creation of a surgical portal while still obtaining a desirable portal size. Because the wedge expander has a pyramidal shape, the rods expand in a lateral direction depicted by arrow 953 as the wedge expander advances further. When a desired amount of rod retraction is achieved, a retaining ring similar to that described above may be used to maintain the portal size upon removal of the expander. In one particular application of this method, a posterior rod is fixed so that as wedge expander 900 is advanced, the other rods move relative to the posterior rod. This ensures expansion occurs in a unilateral direction within the body, and protecting any sensitive tissue behind, i.e., posterior to, the posterior rod.

Expansion Handle

Figure 33:
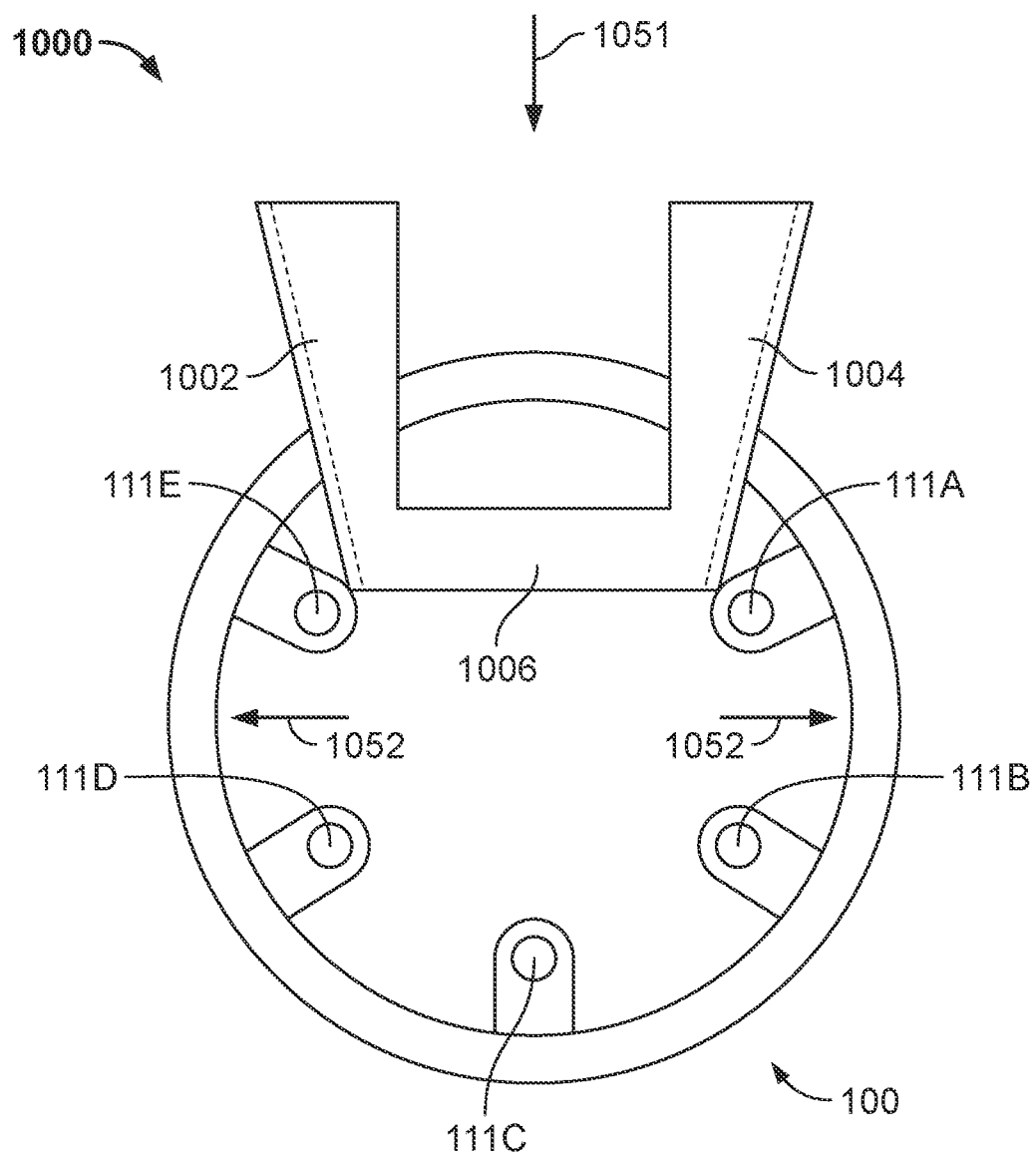
FIG. 33 is a top view of an expansion block according to another embodiment of the present disclosure.

Yet another aspect of the disclosure is an expansion handle. In one embodiment shown in FIG. 33, expansion handle 1000 is generally U-shaped with wings 1002, 1004 and a link portion 1006. Each wing flares outward from link portion 1006 to a free end. A method of using the expansion handle involves preparing a surgical site with a retractor system 100. Expansion handle 1000 is then advanced toward the retractor system as indicated by arrow 1051 so that link portion 1006 passes between rods 111A, 111E. As expansion handle 1000 advances further, the flaring feature of wings 1002, 1004 cause rods 111A, 111E to be displaced in a lateral direction 1052, thereby increasing the surgical portal size. The flared shape of expansion handle 1000 allows for incremental expansion of the rods, thus allowing for safer creation of a surgical portal while still obtaining a desirable portal size.

Other Expanders

Figure 34A:
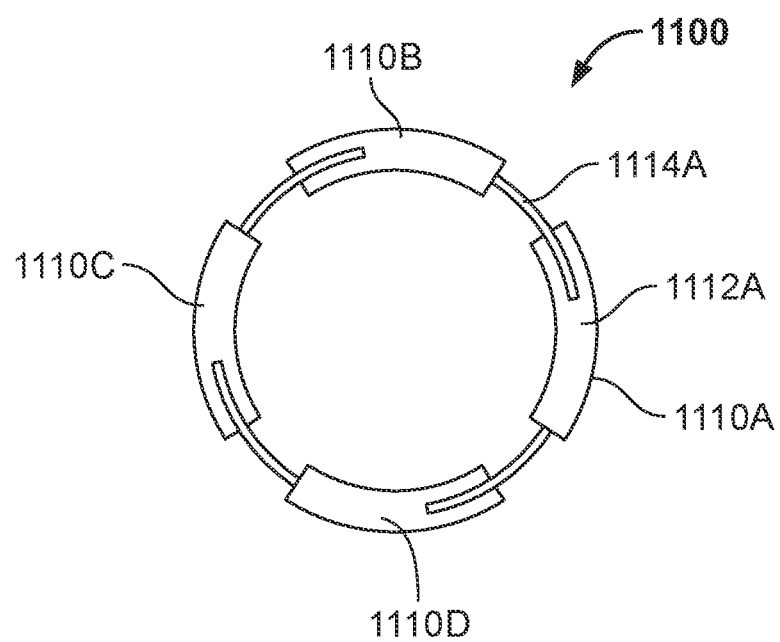
FIGS. 34A-B are top and side views of an overlapping plate expander according to one embodiment of the present disclosure.
Figure 34B:
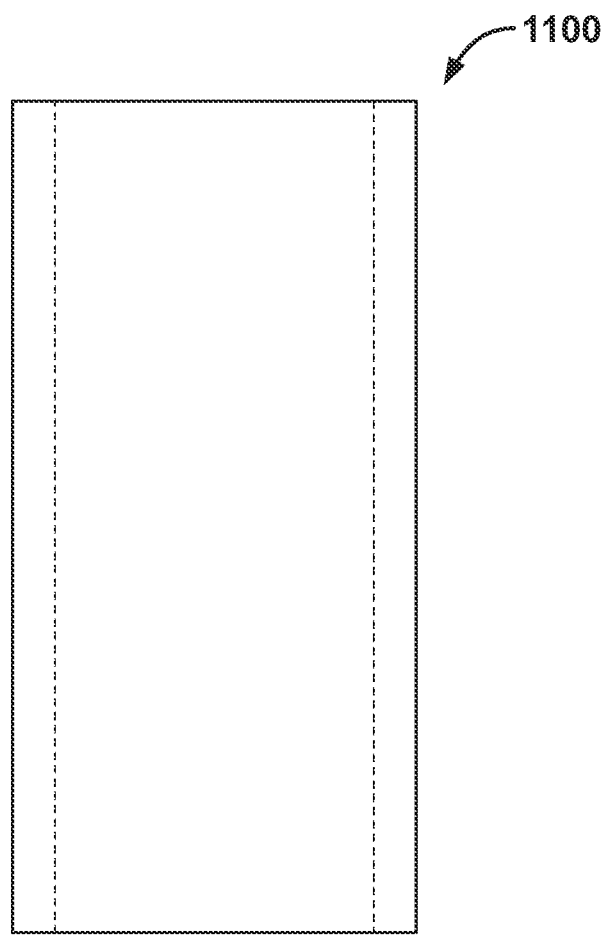

In yet another embodiment, an expander can be constructed from a series of plates with varying thickness as shown in FIGS. 34A-B. Overlapping plate expander 1100 includes a plurality of plates 1110A-D. Each plate includes a thick portion and a thin portion, such as portions 1112A and 1114A, respectively, of plate 1110A, for example. Each thick portion includes an opening at an end opposite the thin portion sized so that a thin portion from an adjacent plate fits therein.

Figure 35A:
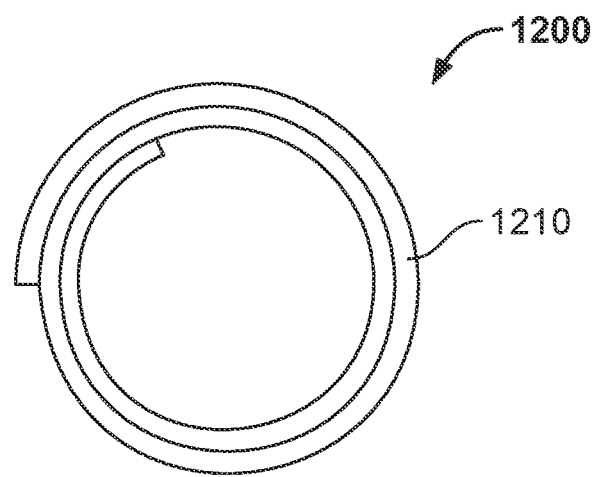
FIGS. 35A-B are top and side views of a spiral expander according to one embodiment of the present disclosure.
Figure 35B:
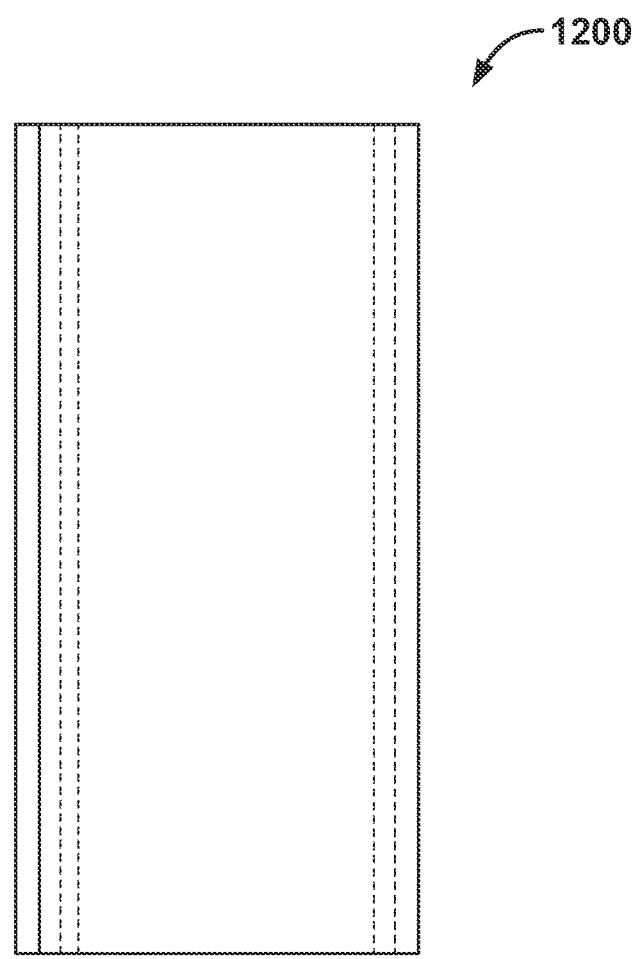
Figure 36:
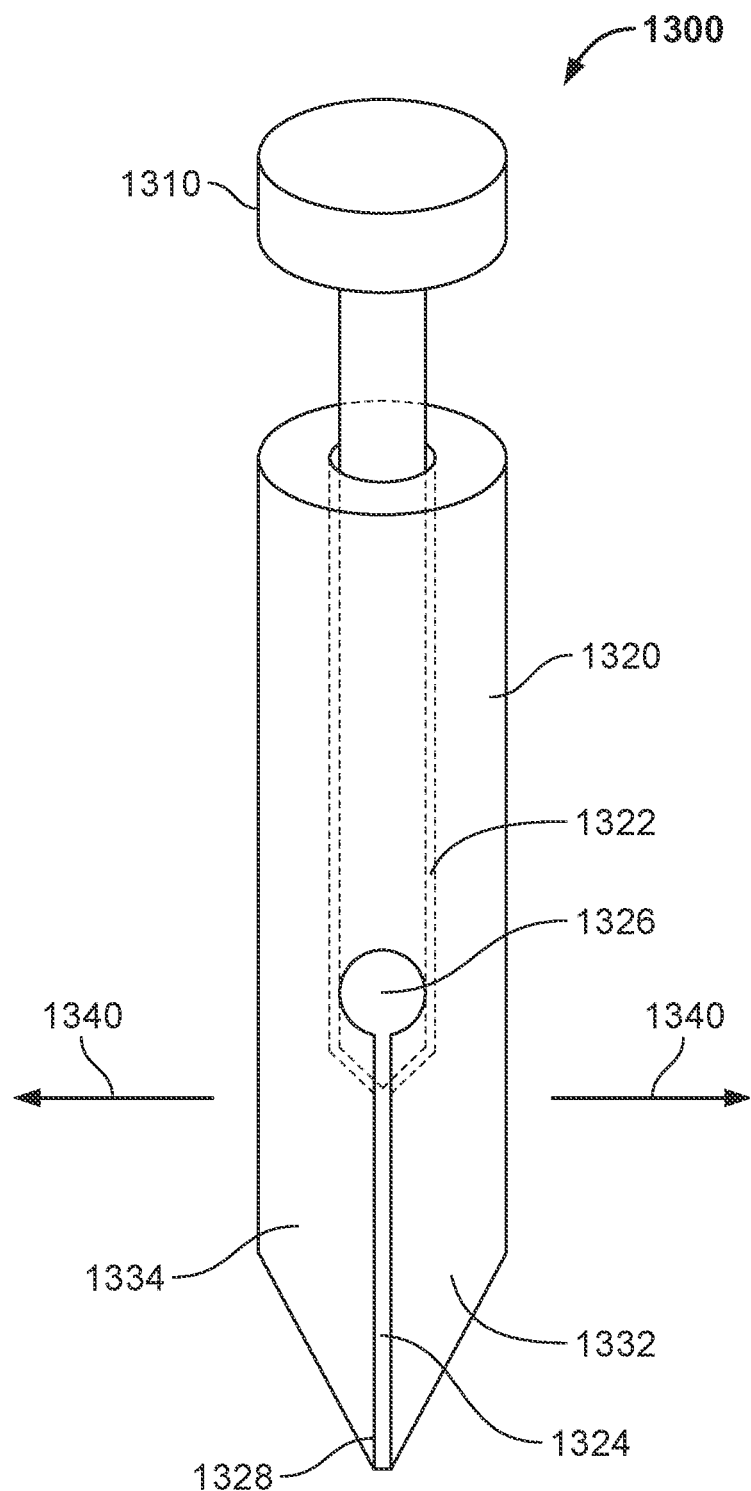
FIG. 36 is a perspective view of a two-component uniaxial expander according to one embodiment of the present disclosure.

Another embodiment of an expander is depicted in FIGS. 35A-B. Spiral expander 1200 includes a coil spring 1210 adapted to wind and unwind to change its overall outer diameter. FIG. 36 shows yet another embodiment in the form of a two-component uniaxial expander 1300. The uniaxial expander includes an actuator 1310 and a body 1320. The actuator 1310 is sized to fit within a cavity 1322 of the body. Cavity 1322 extends from one end and tapers toward at an interior location in the body. From the interior end of the cavity extends a slot 1324 having a smaller cross-sectional area than the cavity. An interior end of slot 1324 includes a hole 1326 as shown to function as a pivot point for arms 1332, 1334, so that the arms can move apart, as described in greater detail below. Opposite actuator 1310 is a tapering tip 1328 of body 1320.

In other embodiments, the expander is designed to expand hydraulically, pneumatically, or by other mechanical means such as via a collet. One example of a hydraulic expander is a bladder ring. The ring would hold liquid therein so that the ring will expand or contract radially with changes in pressure within the ring. Similar principles would apply to a pneumatic expander. The expander could also be a two-component structure with a taper screw and collet. In this manner, the structure is configured to expand or contract with actuation of the taper screw.

In one use of the overlapping plate expander, spiral expander, and others, the applicable expander is inserted into a surgical portal between rods of a retractor in a closed position. When the expander is advanced to a desired position in the portal, the applicable expander is caused to expand based on the applicable expansion mechanism. For example, the overlapping plate expander can be pushed apart by hand or with a tool where the plates include features connected to an attachment point for the tool. Then, actuation of the tool causes the plates to spread apart. The spring expander can be held closed, i.e., compressed, during insertion and then unwind and expand upon release. With regard to the uniaxial expander, a difference in size between the opening and the slit is such that the actuator fits within the opening but must push against sides of the slit as it is advanced further into the body of the expander. Thus, in a method of using the uniaxial expander, the body is first inserted in between the rods with the actuator in a withdrawn position, then the actuator is pressed down to cause arms at the end of the expander to distract in opposite directions on the same axis, as indicated by reference numeral 1340. In other examples, the screw of the collet expander can be rotated to cause a radial dimension of the collet to increase while pressure can be applied into hydraulic or pneumatic expander bodies to cause radial expansion.

Each of the above described expanders, although described for use in distracting tissue to create a portal, may also be used specifically for tissue retention within a previously created tissue portal. In these instances, the same design principles as described above are applicable, although the length of the expander will typically be much shorter and will resemble a ring. In this manner, retention can be focused on a distal portion of the portal near the surgical site. One advantage of maintaining tissue retention with rings is it allows a surgeon a larger working area above the ring since the tissue provides some give. This is in contrast to a retention to be extending through a depth of the portal, which would limit access to the inner walls of the tube. Another advantage of using rings for tissue retention is that with the right size and placement, the rings can be used to "toe out" the portal. Various ring shapes and methods of using such rings are described in the '228 Publication and in U.S. Pat. No. 8,992,558, and such concepts are contemplated for use with the methods described in this disclosure. Additionally, structures in the above referenced disclosures may be modified by features of the various embodiments of the present disclosure.

Variations

Each expander or expander component described above may vary in shape as a matter of design choice. Expanders may be rectangular, polygonal, oblong, D-shaped, oval, and many other shapes to correspond with a desired surgical portal shape. Additionally, the grooves or other recesses on a surface of the expanders or components thereof may vary in size or number as needed to accommodate particular rod or blade types and quantity. Materials and accessories, such as lighting and marking, as described for certain embodiments, may also be used in other embodiments as a matter of design choice.

Neuromonitoring

Any of the above embodiments may incorporate neuromonitoring, such as that described in the '228 Publication. For instance, a probe or a rod of a retractor initially inserted into the body and advanced to a target site may include an electrode to detect nerves during advancement of the retractor. The electrode may be positioned on the rod or probe in an offset manner so that where it rotates during insertion, it may detect nerves in multiple directions. Such concepts may be extended to the expanders as described herein, through placement of electrodes on expander structures. Such use may be applicable where rods expanded by such expander structures do not include electrodes and where radial expansion of a portal beyond a starting position is significant.

Lateral Access Alignment Guide and Rigid Arm

The structures, systems and methods as described herein may be used in surgical settings where a retractor holding rods intended for expansion is supported by the rigid arm or frame of the '780 Application. Additionally, alignment to determine an insertion location for inserting the same rods into the body may be performed using an alignment guide described in the '780 Application.

Independent Rod Suspension

The structures, systems and methods as described herein may be used to expand rods of a retractor where at least one rod varies in shape in response to changes in loading on the rod. Details of such rods forming part of a retractor assembly are described in the '841 Application.

Lateral Access Bridges, Shims and Lighting Including Rod Lighting

The structures, systems and methods as described herein may be part of a surgical procedure where after the surgical portal is fully expanded, bridges designed to maintain the portal size and shape and to provide light to the portal may be inserted to improve and enhance the surgical procedure, such as those described in the '796 and '579 Applications. Rods, shims and other retractor components may also be used as described in the '579 Application.

Although the disclosure herein has been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. An expander for use in forming a surgical portal comprising:
   a first member including a first groove on an outer surface configured to engage a retractor and defining a slot; and
   a second member slidably attached to the first member including a second groove on an outer surface configured to engage the retractor and a protrusion configured to fit within the slot, wherein
   the second member is slidable with respect to the first member to change a cross-section of a portion of the expander and the retractor,
   the second member defines a portion of an outer surface of the expander, and
   the expander has a maximum cross-section that includes both the first member and the second member.

2. The expander of claim 1, wherein a second surface of the second member is flush with a first surface of the first member, the second surface being linearly slidable relative to the first surface to change the cross-section of the portion of the expander.

3. The expander of claim 1, wherein the second member includes a sliding portion and a lateral portion, the lateral portion translating laterally when the sliding portion slides with respect to the first member.

4. An expander for use in forming a surgical portal comprising:
   a first member including a first groove on an outer surface configured to engage a retractor and defining a slot; and
   a second member slidably attached to the first member including a second groove on an outer surface configured to engage the retractor and a protrusion configured to fit within the slot, wherein
   the second member is slidable with respect to the first member to change a cross-section of a portion of the expander and the retractor,
   the second member defines a portion of an outer surface of the expander, and
   the expander has a maximum cross-section that includes both the first member and the second member, wherein the protrusion of the second member is within the slot, a position of the protrusion relative to an end of the slot changing with sliding of the second member relative to the first member.

5. An expander extending from a trailing end to a leading end and for use in providing surgical access, the expander comprising:
   a first member including a first groove on an outer surface configured to engage a retractor and defining a slot; and
   a second member attached to the first member including a second groove on an outer surface configured to engage the retractor and a protrusion configured to fit within the slot, the second member being translatable relative to the first member such that translation of the second member relative to the first member causes a change in a cross-section of the retractor and the expander over at least a portion of the expander, wherein the second member is translatable to a first position relative to the first member so that at least a portion of the trailing end of the expander includes the second member.

6. The expander of claim 5, wherein the second member is translatable to a second position relative to the first member so that the expander has a maximum cross-sectional dimension adjacent to the leading end of the expander.

7. The expander of claim 5, wherein when the second member is in the first position relative to the first member, the expander has a maximum cross-sectional dimension at the trailing end of the expander.

8. The expander of claim 5, wherein the expander has a maximum cross-sectional dimension at a first location between the trailing end and the leading end such that at least part of an outward facing surface of the expander at the first location is defined by an outward facing surface of the second member.

9. The expander of claim 5, wherein when the second member is translated away from the leading end of the expander, a cross-sectional dimension of the expander at the leading end of the expander increases.

10. The expander of claim 5, wherein the expander has a maximum outer dimension at a first minimum distance from the leading end of the expander when the second member is in the first position, the maximum outer dimension being at a second minimum distance from the leading end of the expander when the second member is translated toward the leading end of the expander, the second minimum distance being less than the first minimum distance.

11. The expander of claim 5, wherein a second surface of the second member is flush with a first surface of the first member, the second surface being linearly translatable relative to the first surface to change the cross-section over the at least part of the expander.

12. An expander for providing surgical access comprising:
   a first member with a first surface including a first groove configured to engage a retractor and defining a slot; and
   a second member slidably attached to the first member so that a protrusion on the second member fits within the slot, the second member including a second surface flush with the first surface over at least a portion of a length of the second member and including a second surface including a first groove configured to engage the retractor,
   wherein the second member is slidable with respect to the first member to change a cross-section of a portion of the expander and the retractor.

13. The expander of claim 12, wherein the second member is slidable with respect to the first member along a longitudinal axis of the expander.

14. The expander of claim 13, wherein the second member is slidable with respect to the first member to change an extent of overlap between the first surface and the second surface.

15. The expander of claim 12, wherein the length of the second member is a maximum dimension of the second member.

* * * * *